US012274307B2

(12) United States Patent
Nakano et al.

(10) Patent No.: US 12,274,307 B2
(45) Date of Patent: Apr. 15, 2025

(54) AEROSOL GENERATING DEVICE, METHOD OF CONTROLLING AEROSOL GENERATING DEVICE, AND PROGRAM

(71) Applicant: Japan Tobacco Inc., Tokyo (JP)

(72) Inventors: Takuma Nakano, Tokyo (JP); Manabu Yamada, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 157 days.

(21) Appl. No.: 18/071,644

(22) Filed: Nov. 30, 2022

(65) Prior Publication Data

US 2023/0109789 A1 Apr. 13, 2023

Related U.S. Application Data

(63) Continuation of application No. 16/548,844, filed on Aug. 23, 2019, now Pat. No. 11,547,146, which is a
(Continued)

(51) Int. Cl.
*A24F 40/50* (2020.01)
*A24B 15/167* (2020.01)
(Continued)

(52) U.S. Cl.
CPC ............ *A24F 40/50* (2020.01); *A24B 15/167* (2016.11); *A24F 40/44* (2020.01); *A24F 40/51* (2020.01); *A24F 40/10* (2020.01)

(58) Field of Classification Search
CPC ........ A24B 15/167; A24F 40/50; A24F 40/51; A24F 40/10; A24F 40/44; A61M 11/042; A61M 2016/0021; A61M 2205/50
See application file for complete search history.

(56) References Cited

U.S. PATENT DOCUMENTS 10,111,465 B2 * 10/2018 Liu .................... A24F 40/40
10,201,186 B2 * 2/2019 Alarcon ............. H05B 1/0227
(Continued)

FOREIGN PATENT DOCUMENTS

CN 104736005 A 6/2015
CN 105208884 A 12/2015
(Continued)

OTHER PUBLICATIONS

International Search Report and Written Opinion mailed on Aug. 1, 2017 for PCT/JP2017/016133 filed on Apr. 24, 2017, 11 pages including English Translation of the International Search Report.
(Continued)

*Primary Examiner* — Abdullah A Riyami
*Assistant Examiner* — Thang H Nguyen
(74) *Attorney, Agent, or Firm* — XSENSUS LLP

(57) ABSTRACT

An is an aerosol generating device which is capable of generating an aerosol at an appropriate timing includes: a power source which supplies power in order to atomize an aerosol source and/or heat a flavor source; a sensor which outputs a measurement value for controlling the power supplied; and a controller which controls the power supplied on the basis of the measurement value. The controller controls a power supply amount from the power source to be a first value when the measured value is equal to or larger than a first threshold and smaller than a second threshold larger than the first threshold, and the power supply amount to be larger than the first value when the measured value is equal to or larger than the second threshold.

6 Claims, 16 Drawing Sheets

Related U.S. Application Data continuation of application No. PCT/JP2017/016133, filed on Apr. 24, 2017.

(51) Int. Cl.
*A24F 40/10* (2020.01)
*A24F 40/44* (2020.01)
*A24F 40/51* (2020.01)

(56) References Cited

U.S. PATENT DOCUMENTS

| | | | | |
|---|---|---|---|---|
| 10,736,356 | B2* | 8/2020 | Jordan | A24F 40/50 |
| 2012/0080107 | A1* | 4/2012 | Kruglick | A61L 9/205 |
| | | | | 422/108 |
| 2014/0299141 | A1* | 10/2014 | Flick | H05B 1/0202 |
| | | | | 219/494 |
| 2016/0057811 | A1* | 2/2016 | Alarcon | H05B 1/0227 |
| | | | | 219/494 |
| 2016/0206003 | A1* | 7/2016 | Yamada | H05B 1/0202 |
| 2017/0079329 | A1* | 3/2017 | Zitzke | H05B 1/0225 |
| 2017/0108840 | A1* | 4/2017 | Hawes | A24F 40/50 |
| 2017/0238596 | A1 | 8/2017 | Matsumoto et al. | |
| 2018/0042308 | A1* | 2/2018 | Takeuchi | A24F 40/60 |
| 2018/0116283 | A1* | 5/2018 | Rostami | H05B 1/0244 |
| 2018/0220697 | A1* | 8/2018 | Fariss | A24F 40/40 |
| 2019/0364970 | A1* | 12/2019 | Choukroun | A24F 40/53 |

FOREIGN PATENT DOCUMENTS

| | | |
|---|---|---|
| DE | 10 2009 029 768 A1 | 1/2011 |
| EP | 2047880 A1 | 4/2009 |
| EP | 2460423 A1 | 6/2012 |
| EP | 2915443 A1 | 9/2015 |
| EP | 2871984 B1 | 9/2016 |
| GB | 2519101 A | 4/2015 |
| JP | 2013-541373 A | 11/2013 |
| JP | 2013-545474 A | 12/2013 |
| JP | 2014-534814 A | 12/2014 |
| JP | 2017-046700 A | 3/2017 |
| WO | 2013/060784 A2 | 5/2013 |
| WO | 2014/054035 A1 | 4/2014 |
| WO | 2014/150247 A1 | 9/2014 |
| WO | 2016/075746 A1 | 5/2016 |
| WO | 2016/091658 A1 | 6/2016 |
| WO | 2016/118645 A1 | 7/2016 |
| WO | 2016/175320 A1 | 11/2016 |

OTHER PUBLICATIONS

International Search Report and Written Opinion mailed on Aug. 1, 2017 for PCT/JP2017/016134 filed on Apr. 24, 2017, 11 pages including English Translation of the International Search Report.
International Search Report and Written Opinion mailed on Aug. 1, 2017 for PCT/JP2017/016135 filed on Apr. 24, 2017, 13 pages including English Translation of the International Search Report.
Notification of Reasons for Refusal received for Japanese Patent Application No. 2019-514884, dated May 9, 2019, 9 bages including English Translation.
Notification of Reasons for Refusal received for Japanese Patent Application No. 2019-514885, dated May 15, 2019, 9 bages including English Translation.
Notification of Reasons for Refusal received for Japanese Patent Application No. 2019-514886, dated May 8, 2019, 8 bages including English Translation.
Taiwanese Office Action issued on Aug. 20, 2019 in corresponding Taiwanese Patent Application No. 106113597, with machine generated English translation, 18 pages.
Japanese Office Action dated Sep. 30, 2019 issued in corresponding Japanese Patent Application No. 2019-514886 (with English Translation), 15 pages.
Partial supplementary European search report dated Jul. 6, 2020, issued in corresponding European patent application No. 17907564.3.
Office Action issued on Mar. 11, 2021, in corresponding Korean patent Application No. 10-2019-7023448, 12 pages.
Office Action issued on Aug. 4, 2021 in corresponding Chinese patent Application No. 201780088535.0.
German Office Action issued on Dec. 16, 2021 in corresponding German patent Application No. 11 2017 007 475.4.
German Office Action issued on Dec. 10, 2021 in corresponding German patent Application No. 11 2017 007 473.8.
Office Action issued on Dec. 16, 2021, in corresponding German patent Application No. 112017007474.6, 10 pages.
Office Action issued Apr. 21, 2022 in Japanese Patent Application No. 2021-011108 , 10 pages.
European Office Action issued May 22, 2024 in corresponding European Patent Application No. 17907973.6, 8 pages.

* cited by examiner

AEROSOL GENERATING DEVICE, METHOD OF CONTROLLING AEROSOL GENERATING DEVICE, AND PROGRAM

CROSS REFERENCE TO RELATED APPLICATIONS

This application is a Continuation of U.S. patent application Ser. No. 16/548,844, fled on Aug. 23, 2019, which is a. Continuation of PCT International Application No. PCT/JP2017/016133, filed on Apr. 24, 2017, each of which is hereby expressly incorporated by reference into the present application.

TECHNICAL FIELD

The present disclosure relates to a device which generates aerosol inhaled by a user or aerosol added with flavor, a method of controlling such an aerosol generating device, and a program.

BACKGROUND ART

A glass fiber has been widely used as a wick serving to retain an aerosol source near a heater of an e-cigarette. However, instead of the glass fiber, it is considered to use ceramics for the wick, which can be expected to simplify the manufacturing process and improve the aerosol yield.

The e-cigarette in which the glass fiber is used for the wick is controlled to deliver aerosol into the oral cavity of a user, the aerosol being generated by atomizing an aerosol source by a heater immediately after the inhalation is started, and to stop the generation of this aerosol immediately after the inhalation is stopped, such that an unnatural feeling of the inhalation is not provided to the user. When the wick made of ceramics, e.g., alumina is used, it is necessary to advance the timing at which the energization of the heater is started and the timing at which the energization of the heater is terminated in a single puff (inhalation cycle) to enjoy smoking using the e-cigarette with the same feeling as before, because the typical thermal capacity of the wick made of alumina is about 0008 J/K, which is higher than the typical thermal capacity of about 0.003 J/k in the wick made of glass fiber.

In this regard, there is proposed a technique in which a threshold to determine puff start time is smaller than a threshold to determine puff end time (see PTL 1, for example).

However, when the threshold to determine the puff start time is made small, it is easy to pick up noise, such that unnecessary energization easily occurs.

When the threshold to determine the puff end time is larger than the threshold to determine the puff start time, in the determination made only by comparing the signal and the threshold, the puff end condition is satisfied substantially at the same time as or immediately after the timing when the puff start condition is satisfied.

Furthermore, an appropriate value as a threshold associated with the determination differs depending on the inhalation way, and the inhalation way has differences among individuals.

CITATION LIST

Patent Literature

PTL 1: National Publication of International Patent Application No. 2013-541373

PTL 2: National Publication of International Patent Application No. 2014-534814

PTL 3: International Publication No. WO 2016/118645

PTL 4: International Publication No. WO 2016/175320

SUMMARY OF INVENTION

Technical Problem

The present disclosure has been made in view of the problems described above.

A first object of the present disclosure is to provide an aerosol generating device capable of generating aerosol at an appropriate timing while suppressing unnecessary energization.

A second object of the present disclosure is to provide an aerosol generating device capable of generating aerosol at an appropriate timing.

A third object of the present disclosure is to provide an aerosol generating device capable of optimizing a timing when the aerosol generation is stopped for each user.

Solution to Problem

To achieve the above-described first object, according to a first embodiment of the present disclosure, there is provided an aerosol generating device, comprising a power source that supplies power to perform atomization of an aerosol source and/or heating of a flavor source; a sensor that outputs a measured value for controlling the power supplied; and a controller that controls the power supplied based on the measured value, wherein the controller controls a power supply amount from the power source to be a first value when the measured value is equal to or larger than a first threshold and smaller than a second threshold larger than the first threshold, and the power supply amount to be larger than the first value when the measured value is equal to or larger than the second threshold.

In one embodiment, the aerosol is not generated from the aerosol source or the flavor source by the power supply amount of the first value.

In one embodiment, the controller stops supplying the power when the measured value does not reach a value being equal to or larger than the second threshold within a predetermined time from when the measured value is equal to or larger than the first threshold or supplying the power with the first value is started.

In one embodiment, at least one of power for applying the power supply amount of the first value or an amount of power per unit time and the predetermined time is set so that the first value is equal to or less than the power supply amount for starting the aerosol generation from the aerosol source or the flavor source.

In one embodiment, the power supply amount per unit time when the measured value is equal to or larger than the first threshold and smaller than the second threshold is between zero value and the power supply amount per unit time when the measured value is equal to or larger than the second threshold, and is closer to the latter than the former.

In one embodiment, the controller stops supplying the power when the measured value falls below the third threshold which is equal to or larger than the second threshold.

In one embodiment, the second threshold is closer to the first threshold than the third threshold.

In one embodiment, the second threshold is closer to the third threshold than the first threshold.

In one embodiment, the second threshold is equal to the third threshold.

In one embodiment, a difference between the second threshold and the first threshold is larger than the first threshold.

In one embodiment, a porous body having pores therein is included, the pores being configured to perform transferring the aerosol source and/or the flavor source to a position and/or holding the aerosol source and/(or the flavor source to such a position, wherein the position is a position at which a load can perform atomization and/or heating with the power supplied from the power source.

According to the first embodiment of the present disclosure, there is also provided a method of controlling an aerosol generating device for controlling power supplied from a power source to perform atomization of an aerosol source and/or heating of a flavor source based on a measured value output from a sensor, the method comprising a step of controlling a power supply amount from the power source to be a first value when the measured value is equal to or larger than a first threshold and smaller than a second threshold larger than the first threshold; and a step of controlling the power supply amount to be larger than the first value when the measured value is equal to or larger than the second threshold.

According to the first embodiment of the present disclosure, a program causing a processor to execute the above-described control method is also provided.

According to the first embodiment of the present disclosure, there is also provided an aerosol generating device, comprising a power source that supplies power to perform atomization of an aerosol source and/or heating of a flavor source; a sensor that outputs a measured value for controlling the power supplied; and a controller that controls the power supplied based on the measured value, wherein the controller controls to supply a first power from the power source when the measured value is equal to or larger than a first threshold and smaller than a second threshold larger than the first threshold, and to supply, from the power source, a power larger than the first power when the measured value is equal to or larger than the second threshold.

According to the first embodiment of the present disclosure, there is also provided an aerosol generating device, comprising a power source that supplies power to perform atomization of an aerosol source and heating of a flavor source; a sensor that outputs a measured value for controlling the power supplied; and a controller that controls the power supplied based on the measured value, wherein the controller controls a power supply amount from the power source to be a second value when the measured value exceeds a first threshold, controls to stop supplying the power when the measured value falls below a second threshold larger than the first threshold after the power source supplies the power of the second value, and controls the power supply amount before the measured value exceeds the first threshold to be smaller than the second value.

To achieve the above-described second object, according to a second embodiment of the present disclosure, there is provided an aerosol generating device, comprising a power source that supplies power to perform atomization of an aerosol source and/or heating of a flavor source; a sensor that outputs a measured value for controlling the power supplied; and a controller that controls the power supplied from the power source based on the measured value, wherein the controller controls to increase a power supply amount per unit time (hereinafter referred to as a "unit amount of power supplied") when a first condition that the measured value is equal to or larger than a first threshold is satisfied, and to decrease the unit amount of power supplied when a second condition that the measured value is smaller than a second threshold larger than the first threshold and a third condition which is different from the first condition and the second condition are satisfied.

In one embodiment, the third condition is not satisfied at the same time as the first condition.

In one embodiment, the second condition can be satisfied prior to the third condition.

In one embodiment, the third condition is a condition based on the measured value.

In one embodiment, the third condition is a condition based on a time derivative of the measured value.

In one embodiment, the third condition is a condition that the time derivative of the measured value is smaller than or equal to zero.

In one embodiment, the third condition is a condition that the time derivative of the measured value is equal to or smaller than a third threshold which is smaller than zero.

In one embodiment, the controller increases the unit amount of power supplied when the time derivative of the measured value exceeds zero within a predetermined return period from when the second condition and the third condition are satisfied.

In one embodiment the controller gradually increases the unit amount of power supplied from zero value to a second unit amount of power supplied, and from the second unit amount of power supplied to a third unit amount of power supplied larger than the second unit amount of power supplied when the first condition is satisfied, and increases the unit amount of power supplied from zero value to the third unit amount of power supplied when the time derivative of the measured value exceeds zero within the predetermined return period from when the second condition and the third condition are satisfied.

In one embodiment, the third condition is a condition that the measured value falls below the second threshold after the measured value exceeds a fourth threshold which is equal to or larger than the second threshold.

In one embodiment, the controller decreases the unit amount of power supplied when a condition that the measured value is smaller than the first threshold is satisfied in a case where the third condition is not satisfied within a predetermined determination period from when the first condition is satisfied.

In one embodiment, the controller calculates a maximum value of the measured value every period from when supplying the power is started to when supplying the power is stopped, and updates the fourth threshold based on a plurality of the maximum values calculated.

In one embodiments, the controller updates the fourth threshold based on an average value of the plurality of maximum values calculated.

In one embodiments, the controller updates the fourth threshold based on a weighted average value of the plurality of maximum values calculated, and in the calculation of the weighted average value, a greater weight is assigned to the maximum value calculated for a more recent period from when supplying the power is started to when supplying the power thus started is stopped.

In one embodiment, the controller calculates a maximum value of the measured value every period from when supplying the power is started to when supplying the power is stopped, updates the second threshold based on a plurality of the maximum values calculated, and updates the fourth threshold to be equal to or larger than the updated second threshold.

In one embodiment, the controller stores changes in the measured value every period from when supplying the power is started to when supplying the power is stopped, updates the second threshold based on a plurality of the measured values stored, and updates the fourth threshold to be equal to or larger than the updated second threshold.

In one embodiment, the controller updates the second threshold based on the changes in a plurality of the measured values stored and based on a value obtained by subtracting a specified value from an average value of durations of the changes in the measured values.

In one embodiment, the third condition is a condition that a predetermined dead period has elapsed since the first condition was satisfied.

In one embodiment, the controller calculates at least one of a first required time from when the first condition is satisfied to when the measured value reaches the maximum value and a second required time from when the first condition is satisfied until the first condition is not satisfied, every period from when supplying the power is started to when supplying the power is stopped, and updates the dead period based on at least one of a plurality of the first required times and a plurality of the second required times.

In one embodiment, the controller updates the dead period based on at least one of an average value of a plurality of the first required times and an average value of a plurality of the second required times.

In one embodiment, the controller updates the dead period based on at least one of a weighted average value of a plurality of the first required times and a weighted average value of a plurality of the second required times, and in the calculation of the weighted average value, a greater weight is assigned to at least one of the first required times and the second required times which are calculated for a more recent period from when supplying the power is started to when supplying the power thus started is stopped.

In one embodiment, the controller calculates a maximum value of the measured value every period from when supplying the power is started to when supplying the power is stopped, and updates the second threshold based on a plurality of the maximum values calculated.

In one embodiment, the controller stores a change in the measured value every period from when supplying the power is started to when supplying the power is stopped, and updates the second threshold based on a plurality of the changes in the measured value stored.

In one embodiment, the controller can implement a selection mode in which one or more third conditions are selectable from a third condition group including a plurality of the third conditions.

In one embodiment, in the selection mode, the controller stores the measured values, and selects the one or more third conditions from the third condition group based on the stored measured values.

In one embodiment, in the selection mode, the controller selects the one or more third conditions from the third condition group based on a time derivative of the stored measured values.

In one embodiment, in the selection mode, the controller selects the one or more third conditions from the third condition group based on a maximum value of the stored measured values.

In one embodiment, in the selection mode, the controller selects the one or more third conditions from the third condition group based on durations of the changes in the measured values stored.

In one embodiment, in the selection mode, the controller selects the one or more third conditions from the third condition group based on an operation on the aerosol generating device.

In one embodiment, the controller stores the third condition group in advance.

In one embodiment, the controller acquires the selected one or more third conditions from the third condition group stored outside the aerosol generating device.

In one embodiment, the third condition is a condition that at the time of determining the third condition, a predetermined time or more has elapsed since the measured value output until the third condition is determined became maximum.

In one embodiment, the controller increases the unit amount of power supplied from zero value to a first unit amount of power supplied when the first condition is satisfied.

In one embodiment, the controller decreases the unit amount of power supplied from the first unit amount of power supplied to zero value when the second condition and the third condition are satisfied.

According to the second embodiment of the present disclosure, there is also provided an aerosol generating device, comprising a power source that supplies power to perform atomization of an aerosol source and/or heating of a flavor source: a sensor that outputs a measured value for controlling the power supplied; and a controller that controls the power supplied based on the measured value, wherein the controller controls to increase a power supply amount per unit time (hereinafter referred to as a "unit amount of power supplied") when a first condition that the measured value is equal to or larger than a first threshold is satisfied, and to decrease the unit amount of power supplied when a condition is satisfied, the condition not being satisfied in a predetermined adjustment period from when the first condition is satisfied.

In one embodiment, the adjustment period is equal to or longer than a control period of the controller.

According to the second embodiment of the present disclosure, there is also provided an aerosol generating device, comprising a power source that supplies power to perform atomization of an aerosol source and/or heating of a flavor source; and a controller that controls the power supplied, wherein the controller controls to increase a power supply amount per unit time (hereinafter referred to as a "unit amount of power supplied") when all of one or more conditions included in a first condition group are satisfied, and to decrease the unit amount of power supplied when all of one or more conditions included in a second condition group are satisfied, and the number of conditions included in the first condition group is smaller than the number of conditions included in the second condition group.

In one embodiment each of the first condition group and the second condition group includes at least one condition involving a common variable.

In one embodiment, a sensor that outputs a measured value for controlling the power supplied is included, wherein the common variable is based on the measured value.

In one embodiment, the condition involving a common variable is a condition that an absolute value of the common variable is equal to or larger than a threshold, larger than a threshold, smaller than or equal to a threshold, or smaller than a threshold, and the threshold in the condition involving the common variable included in the first condition group is different from the threshold in the condition involving the common variable included in the second condition group.

In one embodiment, the threshold in the condition involving the common variable included in the first condition group is smaller than the threshold in the condition involving the common variable included in the second condition group.

In one embodiment, a porous body having pores therein is included, the pores being configured to perform transferring the aerosol source and/or the flavor source to a position and/or holding the aerosol source and/or the flavor source to such a position, wherein the position is a position at which a load can perform atomization and/or heating with the power supplied from the power source.

According to the second embodiment of the present disclosure, there is also provided an aerosol generating device, comprising a power source that supplies power to perform atomization of an aerosol source and/or heating of a flavor source; and a controller that controls the power supplied, wherein the controller controls to increase a power supply amount per unit time (hereinafter referred to as a "unit amount of power supplied") when a first condition is satisfied, and to decrease the unit amount of power supplied when a second condition severer than the first condition is satisfied.

In one embodiment, a porous body having pores therein is included, the pores being configured to perform transferring the aerosol source and/or the flavor source to a position and/or holding the aerosol source and/or the flavor source to such a position, wherein the position is a position at which a load can perform atomization and/or heating with the power supplied from the power source.

According to the second embodiment of the present disclosure, there is also provided a method of controlling an aerosol generating device for controlling power supplied from a power source to perform atomization of an aerosol source and/or heating of a flavor source based on a measured value output from a sensor, the method comprising a step of increasing a power supply amount per unit time (hereinafter referred to as a "unit amount of power supplied") when a first condition that the measured value is equal to or larger than a first threshold is satisfied; and a step of decreasing the unit amount of power supplied when a second condition that the measured value is smaller than a second threshold larger than the first threshold and a third condition that is different from the first condition and the second condition are satisfied.

According to the second embodiment of the present disclosure, a program causing a processor to execute the above-described control method is also provided.

According to the second embodiment of the present disclosure, there is also provided a method of controlling an aerosol generating device for controlling power supplied from a power source to perform atomization of an aerosol source and/or heating of a flavor source based on a measured value output from a sensor, the method comprising a step of increasing the power supply amount per unit time (hereinafter referred to as a "unit amount of power supplied") when a first condition that the measured value is equal to or larger than a first threshold is satisfied; and a step of decreasing the unit amount of power supplied when a condition is satisfied, the condition not being satisfied in a predetermined adjustment period from when the first condition is satisfied.

According to the second embodiment of the present disclosure, a program causing a processor to execute the above-described control method is also provided.

According to the second embodiment of the present disclosure, there is also provided a method of controlling an aerosol generating device for controlling power supplied from a power source to perform atomization of an aerosol source and/or heating of a flavor source, the method comprising a step of increasing a power supply amount per unit time (hereinafter referred to as a "unit amount of power supplied") when all of one or more conditions included in a first condition group are satisfied; and a step of decreasing the unit amount of power supplied when all of one or more conditions included in a second condition group are satisfied, wherein the number of conditions included in the first condition group is smaller than the number of conditions included in the second condition group.

According to the second embodiment of the present disclosure, a program causing a processor to execute the above-described control method is also provided.

According to the second embodiment of the present disclosure, there is also provided a method of controlling an aerosol generating device for controlling power supplied from a power source to perform atomization of an aerosol source and/or heating of a flavor source, the method comprising a step of increasing a power supply amount per unit time (hereinafter referred to as a "unit amount of power supplied") when a first condition is satisfied; and a step of decreasing the unit amount of power supplied when a second condition severer than the first condition is satisfied.

According to the second embodiment of the present disclosure, a program causing a processor to execute the above-described control method is also provided.

According to the second embodiment of the present disclosure, there is also provided an aerosol generating device, comprising a power source that supplies power to perform atomization of an aerosol source and/or heating of a flavor source; a sensor that outputs a measured value for controlling the power supplied; and a controller that controls the power supplied based on the measured value, wherein the controller controls to increase a power supply amount per unit time (hereinafter referred to as a "unit amount of power supplied") when a first condition that the measured value is equal to or larger than a first threshold is satisfied, and to decrease the unit amount of power supplied when a second condition that the measured value is smaller than a second threshold larger than the first threshold is satisfied after a third condition that is different from the first condition and the second condition is satisfied.

According to the second embodiment of the present disclosure, there is also provided a method of controlling an aerosol generating device for controlling power supplied from a power source to perform atomization of an aerosol source and/or heating of a flavor source based on a measured value output from a sensor, the method comprising a step of increasing a power supply amount per unit time (hereinafter referred to as a "unit amount of power supplied") when a first condition that the measured value is equal to or larger than a first threshold is satisfied; and a step of decreasing the unit amount of power supplied when a second condition that the measured value is smaller than a second threshold larger than the first threshold is satisfied after a third condition that is different from the first condition and the second condition is satisfied.

According to the second embodiment of the present disclosure, a program causing a processor to execute the above-described control method is also provided.

To achieve the above-described third object, according to a third embodiment of the present disclosure, there is provided an aerosol generating device, comprising a power source that supplies power to perform atomization of an aerosol source and/or heating of a flavor source; a sensor that outputs a measured value representing a first physical quantity for controlling the power supplied; and a controller that acquires the measured value output from the sensor, stores a profile of the measured value, and controls the supplied power by controlling a second physical quantity which is different from the first physical quantity, based on the acquired measured value and at least part of the stored profile of the measured value.

In one embodiment, the controller stores a profile of the measured value, the profile corresponding to a power supply cycle including a period from when the power source starts supplying the power to when supplying the power is stopped, and controls at least one of a stop and continuity of supplying the power based on at least one of a first profile and a second profile, the first profile being a stored profile of the measured values, and the second profile being an average profile of the measured value derived from a plurality of the first profiles.

In one embodiment, the controller derives a first required time required from the start to the end of changes in the measured value based on at least one of the first profile and the second profile, and controls the power supplied so that supplying the power is stopped at a timing earlier than elapse of the first required time.

In one embodiment, the controller derives a first required time required from the start to the end of changes in the measured value based on at least one of the first profile and the second profile, and controls the power supplied so that the power continues to be supplied for a shorter time than the first required time.

In one embodiment, the controller derives a second required time required from the start of changes in the measured values to when the measured value reaches a maximum value, based on at least one of the first profile and the second profile, and controls the power supplied so that supplying the power is stopped at a timing later than elapse of the second required time.

In one embodiment, the controller derives a second required time required from the start of changes in the measured values to when the measured value reaches a maximum value, based on at least one of the first profile and the second profile, and controls the power supplied so that the power continues to be supplied for a longer time than the second required time.

In one embodiment, the controller derives a first required time required from the start to the end of changes in the measured value and a second required time required from the start of changes in the measured values to when the measured value reaches a maximum value, based on at least one of the first profile and the second profile, and controls the power supplied so that supplying the power is stopped at a timing earlier than elapse of the first required time and later than elapse of the second required time.

In one embodiment, the controller derives a first required time required from the start to the end of changes in the measured value and a second required time required from the start of changes in the measured values to when the measured value reaches a maximum value, based on at least one of the first profile and the second profile, and controls the power supplied so that the power continues to be supplied for a shorter time than the first required time and for a longer time than the second required time.

In one embodiment, the controller is configured to acquire the measured value and a measurement time of the measured value and to be capable of executing a first algorithm for setting a timing when supplying the power is stopped or a period of time in which the power continues to be supplied based on a first feature point in the first profile or the second profile and a second algorithm for setting a timing when supplying the power is stopped or a period of time in which the power continues to be supplied based on a second feature point which is different from the first feature point in the first change or the second change, and executes at least one of the first algorithm and the second algorithm based on deviations among the measurement times of the first feature points in each of a plurality of the first profiles or the second profile.

In one embodiment, the controller executes the first algorithm when values based on the deviations among the plurality of measurement times are smaller than or equal to a threshold.

In one embodiment, the number of possible values of the measurement time of the first feature point is larger than that of possible values of the measurement time of the second feature point.

In one embodiment, the measurement time of the first feature point is later than the measurement time of the second feature point.

In one embodiment, the measured value of the first feature point is smaller than the measured value of the second feature point.

In one embodiment, the first feature point is an end point in the first profile or the second profile.

In one embodiment, the second feature point is a point at which the measured value becomes maximum in the first profile or the second profile.

In one embodiment, the controller controls to increase a power supply amount per unit time (hereinafter referred to as a "unit amount of power supplied") when a first condition that the measured value is equal to or larger than a first threshold is satisfied, and to decrease the unit amount of power supplied when the measured value satisfies at least a second condition that the measured value is smaller than a second threshold larger than the first threshold.

In one embodiment, a porous body having pores therein is included, the pores being configured to perform transferring of the aerosol source and/or the flavor source to a position and/or holding the aerosol source and/or the flavor source to such a position, wherein the position is a position at which a load can perform atomization and/or heating with the power supplied from the power source.

According to the third embodiment of the present disclosure, there is also provided a method of controlling an aerosol generating device for controlling power supplied from a power source to perform atomization of an aerosol source and/or heating of a flavor source based on a measured value output from a sensor, the method comprising a step of acquiring the measured value representing a first physical quantity and storing a profile of the measured value; and a step of controlling the supplied power by controlling a second physical quantity which is different from the first physical quantity, based on the acquired measured value and at least part of the stored profile of the measured value.

According to the third embodiment of the present disclosure, a program causing a processor to execute the above-described control method is also provided.

According to the third embodiment of the present disclosure, there is also provided an aerosol generating device, comprising a power source that supplies power to perform atomization of an aerosol source and/or heating of a flavor source; a sensor that outputs a measured value for controlling the power supplied; and a controller that controls the power supplied from the power source based on the measured value and stores a profile of the measured value, wherein the controller controls to increase a power supply amount per unit time (hereinafter referred to as a "unit amount of power supplied") when a first condition that the measured value is equal to or larger than a first threshold is satisfied, and to decrease the unit amount of power supplied when at least a second condition that the measured value is smaller than a second threshold larger than the first threshold is satisfied, and one of the first threshold and the second threshold is a constant value, and the other of the first threshold and the second threshold is an updatable value based on at least part of a profile of the measured value stored by the controller.

In one embodiment, the first threshold is a constant value, and the second threshold is an updatable value based on at least part of a profile of the measured value stored by the controller.

In one embodiment, a porous body having pores therein is included, the pores being configured to perform transferring the aerosol source and/or the flavor source to a position and/or holding the aerosol source and/or the flavor source to such a position, wherein the position is a position at which a load can perform atomization and/or heating with the power supplied from the power source.

According to the third embodiment of the present disclosure, there is also provided a method of controlling an aerosol generating device for controlling power supplied from a power source to perform atomization of an aerosol source and/or heating of a flavor source based on a measured value output from a sensor, the aerosol generating device controlling to increase a power supply amount per unit time (hereinafter referred to as a "unit amount of power supplied") when a first condition that the measured value is equal to or larger than a first threshold is satisfied, and to decrease the unit amount of power supplied when at least a second condition that the measured value is smaller than a second threshold larger than the first threshold is satisfied, the method comprising a step of storing a profile of the measured value; and a step of updating one of the first threshold and the second threshold based on at least part of the stored profile of the measured value.

According to the third embodiment of the present disclosure, a program causing a processor to execute the above-described control method is also provided.

According to the third embodiment of the present disclosure, there is also provided an aerosol generating device, comprising a power source that supplies power to perform atomization of an aerosol source and/or heating of a flavor source; a sensor that outputs a measured value for controlling the power supplied; and a controller that controls the power supplied from the power source based on the measured value, wherein the controller controls to increase a power supply amount per unit time (hereinafter referred to as a "unit amount of power supplied") when a first condition that the measured value is equal to or larger than a first threshold is satisfied, and to decrease the unit amount of power supplied when at least a second condition that the measured value is smaller than a second threshold larger than the first threshold is satisfied, and an update frequency of the first threshold is different from that of the second threshold.

In one embodiment, the update frequency of the first threshold is lower than that of the second threshold.

In one embodiment, a porous body having pores therein is included, the pores being configured to perform transferring the aerosol source and/or the flavor source to a position and/or holding the aerosol source and/or the flavor source to such a position, wherein the position is a position at which a load can perform atomization and/or heating operating with the power supplied from the power source.

According to the third embodiment of the present disclosure, there is also provided a method of controlling an aerosol generating device for controlling power supplied from a power source to perform atomization of an aerosol source and/or heating of a flavor source based on a measured value output from a sensor, the aerosol generating device controlling to increase a power supply amount per unit time (hereinafter referred to as a "unit amount of power supplied") when a first condition that the measured value is equal to or larger than a first threshold is satisfied, and to decrease the unit amount of power supplied when at least a second condition that the measured value is smaller than a second threshold larger than the first threshold is satisfied, the method comprising a step of updating one of the first threshold and the second threshold at different frequencies than the other.

According to the third embodiment of the present disclosure, a program causing a processor to execute the above-described control method is also provided.

According to a third embodiment of the present disclosure, there is also provided an aerosol generating device, comprising a power source that supplies power to perform atomization of an aerosol source and/or heating of a flavor source; a sensor that outputs a measured value representing a first physical quantity for controlling the power supplied; and a controller that controls power supplied from the power source by controlling a second physical quantity which is different from the first physical quantity, based on the measured value, and stores a profile of the measured value, the profile corresponding to a power supply cycle including a period from when supplying the power is started to when supplying the power is stopped, wherein the controller controls the power supplied in an N-th power supply cycle based on a profile of the measured value, the profile corresponding to one or more power supply cycles of an N-1st power supply cycle and power supply cycles before the N-1st power supply cycle (N is a natural number of 2 or more).

In one embodiment, a porous body having pores therein is included, the pores being configured to perform transferring the aerosol source and/or the flavor source to a position and/or holding the aerosol source and/or the flavor source to such a position, wherein the position is a position at which a load can perform atomization and/or heating with the power supplied from the power source.

According to the third embodiment of the present disclosure, there is also provided a method of controlling an aerosol generating device for controlling power supplied from a power source by controlling a second physical quantity which is different from a first physical quantity to perform atomization of an aerosol source and/or heating of a flavor source, based on a measured value representing the first physical quantity output from a sensor, the method comprising a step of storing a profile of the measured value, the profile corresponding to a power supply cycle including a period from when the power source starts supplying the power to when supplying the power is stopped; and a step of controlling the power supplied in an N-th power supply cycle based on a profile of the measured value, the profile corresponding to one or more power supply cycles of an N-1st power supply cycle and power supply cycles before the N-1st power supply cycle (N is a natural number of 2 or more).

According to the third embodiment of the present disclosure, a program causing a processor to execute the above-described control method is also provided.

Advantageous Effects of Invention

According to the first embodiment of the present disclosure, an aerosol generating device can be provided, which can generate aerosol at an appropriate timing while suppressing unnecessary energization.

According to the second embodiment of the present disclosure, an aerosol generating device can be provided, which can stop generating aerosol at an appropriate timing.

According to the third embodiment of the present disclosure, an aerosol generating device can be provided, which can optimize a timing when the aerosol generation is stopped for each user.

DESCRIPTION OF EMBODIMENTS

Hereinafter, embodiments of the present disclosure will be described in detail with reference to drawings.

Incidentally, in the following description, the ordinal terms such as "first," "second," "third," etc. are used for convenience only to distinguish one element having a certain name from another element having a same name. For example, an element modified with an ordinal term of "first" described in the specification and the drawings and the same element modified with the ordinal term of "first" described in claims do not identify a same object in some cases. On the contrary, for example, an element modified with an ordinal term of "second" described in the specification and the drawings and the same element modified with the ordinal term of "first" described in claims identify a same object in some cases. Accordingly, it should be noted that the object identified by such a term should be identified by a name other than the ordinal term.

The following description is merely illustrative of embodiments of the present disclosure. Accordingly it should be noted that the present invention is not limited to the following description, and various changes may be made without departing from the spirit and the scope of the present invention.

Figure 1:
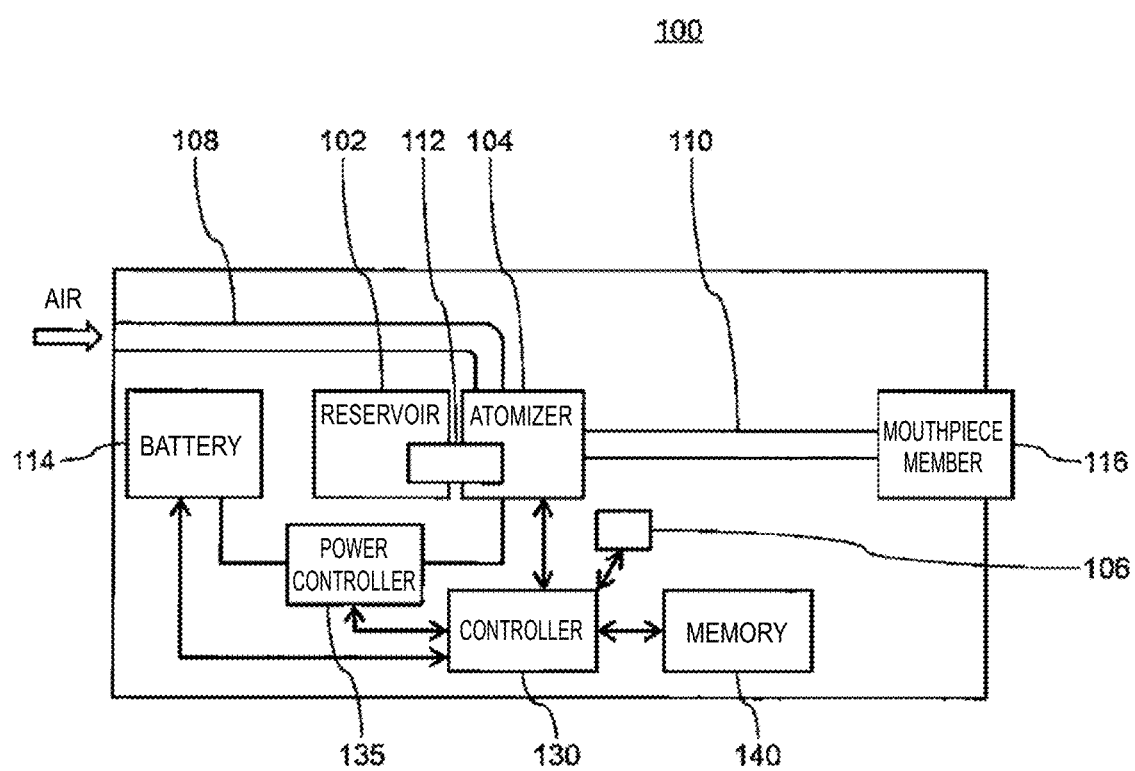
FIG. 1 is a block diagram of an exemplary aerosol generating device 100 according to an embodiment.

1 Exemplary Aerosol Generating Device 100 According to an Embodiment of the Present Disclosure FIG. 1 is a block diagram of an aerosol generating device 100 according to an embodiment of the present disclosure. It should be noted that FIG. 1 schematically and conceptually illustrates each element included in the aerosol generating device 100, but does not intend to indicate the exact arrangement, shape, dimension, positional relationship and the like of each element and the aerosol generating device 100.

As illustrated in FIG. 1, the aerosol generating device 100 includes a reservoir 1021 an atomizer 104, an inhalation sensor 106, an air intake flow path 108, an aerosol flow path 110, a wick 112, a battery 114, and a mouthpiece member 116. Among these elements in the aerosol generating device 100, some elements may be collectively provided as a removable cartridge. For example, the cartridge provided by integrating the reservoir 102 and the atomizer 104 may be configured to be removable in the aerosol generating device 100.

The reservoir 102 may store the aerosol source. For example, the reservoir 102 may be formed of a fibrous or porous material, and may store the aerosol source as a liquid in the interstices between fibers or the pores of the porous material. The reservoir 102 may be configured as a tank for containing the liquid. The aerosol source may be a polyhydric alcohol such as glycerin and propylene glycol, a liquid containing an extract such as a nicotine component originated from the tobacco raw material, a liquid containing any agent, or the like. Particularly, the present invention is applicable to a medical nebulizer or the like, and in this case, the aerosol source may contain a medicinal agent. The reservoir 102 has a configuration in which the aerosol source can be replenished or is configured to be replaceable when the aerosol source is consumed. It should be noted that the aerosol source may mean a flavor source or may include the flavor source. Furthermore, it should be noted that a plurality of reservoirs 102 may be provided, each holding a different aerosol source. Note that the aerosol source may be in a solid state.

The atomizer 104 is configured to atomize the aerosol source to generate the aerosol. The atomizer 104 generates the aerosol when inhalation action is detected by the inhalation sensor 106 (for example, a pressure or flow sensor which detects a pressure or a flow rate of the air intake flow path 108 or the aerosol flow path 110). Note that, in addition to the pressure or flow sensor, an operation button operable by a user can be provided to actuate the atomizer 104.

More specifically, in the aerosol generating device 100, parts of the wick 112 are configured to extend to the reservoir 102 and the atomizer 104, respectively so that a part of the wick 112 connects between the reservoir 102 and the atomizer 104. The aerosol source is carried from the reservoir 102 to atomizer 104 by the capillary effect (action) produced in the wick, and is at least temporarily held in the wick. The atomizer 104 includes a heater (load) (not illustrated) which is electrically connected to a battery 114 so that power supplied to the heater is controlled by a controller 130 and a power controller 135 which are described later. The heater is disposed to be in contact with or in proximity with the wick 112, and is configured to heat and atomize the aerosol source transferred through the wick 112. Note that although a glass fiber has been conventionally used as the wick 112, the controller 130 can control to supply the aerosol at the timing according to the feeling of the smoker even when a porous body such as ceramics having high specific heat is used as the wick 112. Here, the porous body has pores therein, the pores being configured to perform transferring the aerosol source to a position at which the heater can heat the aerosol source and/or holding the aerosol source at such a position by the capillary effect (action).

The air intake flow path 108 and the aerosol flow path 110 are connected to the atomizer 104. The air intake flow path 108 communicates with the outside of the aerosol generating device 100. The aerosol generated in the atomizer 104 is mixed with air that has been taken in through the air intake flow path 108, and is delivered to the aerosol flow path 110. It should be noted that in the present exemplary action, the mixed fluid of the aerosol generated in the atomizer 104 and the air may be simply referred to as aerosol.

The mouthpiece member 116 is positioned at an end of the aerosol flow path 110 (i.e., on the downstream side of the atomizer 104), and is a member configured to make the aerosol flow path 110 open to the outside of the aerosol generating device 100. The user holds the mouthpiece member 116 to inhale the air containing the aerosol, so that the air containing the aerosol is carried into the mouth of the user.

The aerosol generating device 100 further includes the controller 130, the power controller 135, and a memory 140. In FIG. 1, a line connecting the battery 114 and the power controller 135 and a line connecting the power controller 135 and the atomizer 104 represent power supplied from the battery 114 to the atomizer 104 through the power controller 135. In FIG. 1, a double-headed arrow connecting two elements represents that a signal, data or information is transmitted between the two elements. Note that the aerosol generating device 100 illustrated in FIG. 1 is exemplary and in another aerosol generating device, for at least one set of two elements connected by the double-headed arrow in FIG. 1, the signal, data, or information may not be transmitted between the two elements. Furthermore, in another aerosol generating device, for at least one set of two elements connected by the double-headed arrow in FIG. 1, the signal, data, or information may be transmitted from the one element to the other element.

The controller 130 is an electronic circuit module formed as a microprocessor or a microcomputer. The controller 130 is programmed to control the operation of the aerosol generating device 100 in accordance with a computer-executable instruction stored in the memory 140. The controller 130 receives a signal from the sensor 106 and acquires the above-described pressure or flow rate from the signal. Furthermore, the controller 130 receives a signal from the atomizer 104 and the battery 114, aid acquires heater temperature and remaining battery power from the signal. Furthermore, the controller 130 instructs the power controller 135 to control the power supplied from the battery 114 to the atomizer 104 by controlling the magnitude of at least one of the voltage, current and power over a period of time. Note that controlling by the controller 130 the power supplied includes instructing by the controller 130 the power controller 135 to control the power supplied.

As described above, the power controller 135 controls the power supplied from the battery 114 to the atomizer 104 by controlling the magnitude of at least one of the voltage, current and power over a period of time. For example, a switch (contactor), a DC/DC converter, or the like may be used as the power controller 135, and the power controller 135 can control any one of the voltage, current and power supplied from the battery 114 to the atomizer 104 by using either pulse width modulation (PWM, Pulse Width Modulation) control or pulse frequency modulation (PFM, Pulse Frequency Modulation) control. Note that the power controller 135 is integrated with at least one of the atomizer 104, the battery 114 and the controller 130 in some cases.

The memory 140 is an information storage medium such as a ROM, a RAM, or a flash memory. The memory 140 stores setting data required for control of the aerosol generating device 100 in addition to the computer-executable instruction. The controller 130 can be configured to store, in the memory 140, the data of measured values of the inhalation sensor 106 and the like.

Schematically, the controller 130 controls the power supplied for heating the aerosol source and/or the flavor source, that is, the power to be supplied to at least the heater of the atomizer 104 in accordance with at least a detection result of the inhalation sensor 106.

Hereinafter, the operation of the controller 130 will be described in detail.

2 First Exemplary Operations of Controller 130

Figure 2:
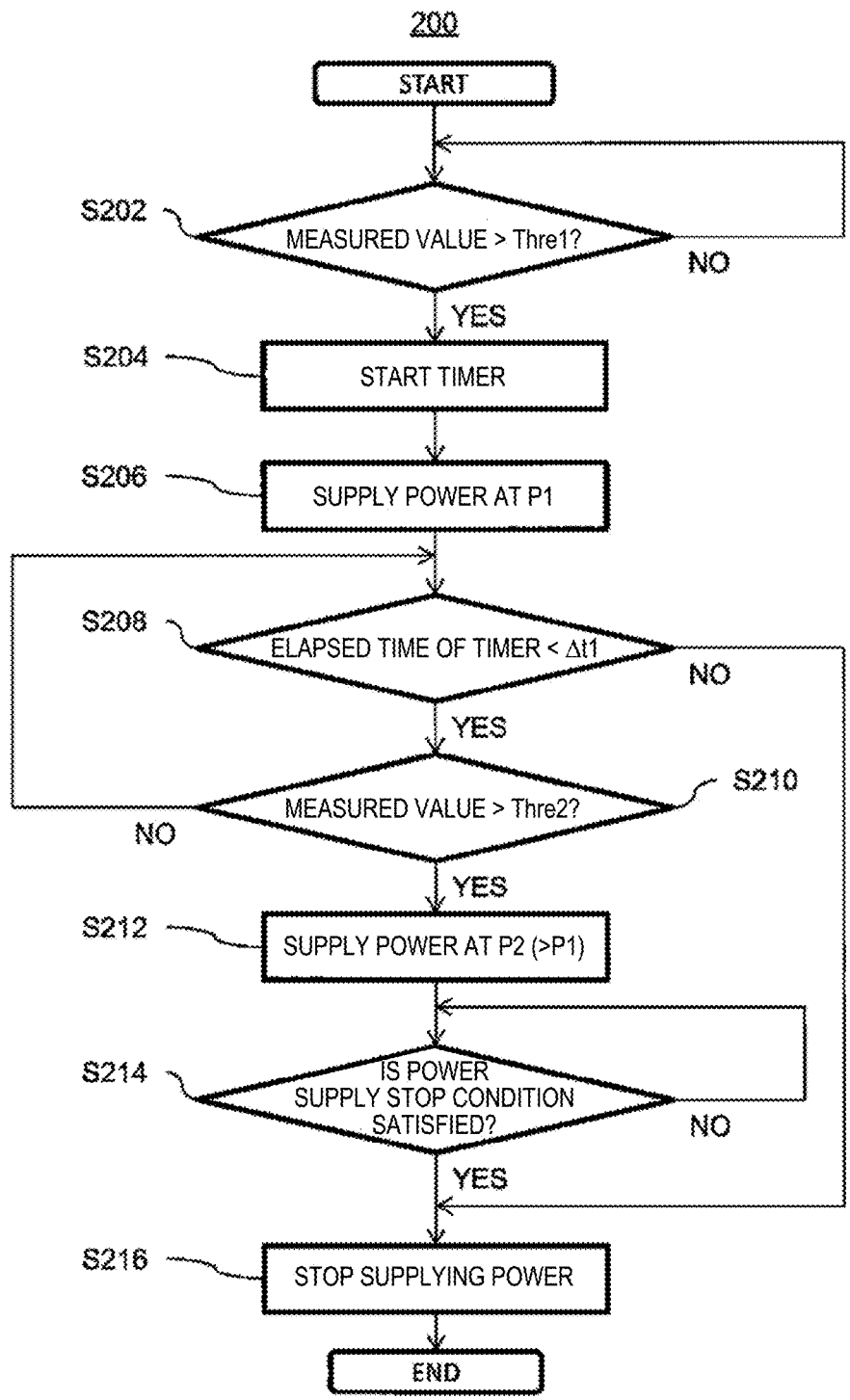
FIG. 2 is a flowchart 200 illustrating first exemplary operations of a controller 130.

FIG. 2 is a flowchart 200 illustrating first exemplary operations of the controller 130.

2-1 Outline of Flowchart 200

Firstly, the outline of the flowchart 200 will be described.

In step S202, the controller 130 determines whether a measured value from the inhalation sensor 106 exceeds a first threshold Thre1. If the measured value exceeds the first threshold Thre1, the process proceeds to step S204, and if no, the process returns to step S202.

In step S204, the controller 130 starts a timer, and in step S206, the controller 130 controls to supply a power Pt to the heater of the atomizer 104 from the power source.

In step S208, the controller 130 determines whether an elapsed time of the timer reaches a predetermined time Δt1. If the elapsed time of the timer does not reach Δt1, the process proceeds to step S210, and if yes, the process proceeds to step S216.

In step S210, the controller 130 determines whether the measured value from the inhalation sensor 106 exceeds a second threshold Thre2 larger than the first threshold Thre1. If the measured value exceeds the second threshold Thre2, the process proceeds to step S212, and if no, the process returns to step S208.

In step S212, the controller 130 controls to supply a power P2 larger than the power P1 to the heater of the atomizer 104 from the power source.

In step S214, the controller 130 determines whether a power supply stop condition is satisfied. If the power supply stop condition is satisfied, the process proceeds to step S216, and if no, the process returns to step S214.

In step S216, the controller 130 stops supplying the power.

2-2 Detail of Flowchart 200

Next, the operations of the flowchart 200 will be described in detail.

2-2-1 Measured Value

In the present exemplary operations, the measured values in steps S202 and S204 each are not a value of a raw signal from the inhalation sensor 106 for example, a voltage value but a value of pressure [Pa] or flow rate [m³/s] obtained from a value of the raw signal, and are intended to be a positive value when the inhalation is performed. The measured value may be a value obtained after the raw signal is filtered by a low-pass filter or the like or a smoothed value such as a simple average value and a moving average value. Note that it is needless to mention that a value of the raw signal from the inhalation sensor 106 may be used as a measured value. In this respect, the same is true for other exemplary operations shown below. Note that as dimensions of the pressure and the flow rate, for example, arbitrary unit systems such as [mmH$_2$O] and [L/min] may be used, respectively.

2-2-2 Threshold

The first threshold Thre1 in step S202 and the second threshold Thre2 in step S210 will be described in detail with reference to FIGS. 3A and 3B.

Reference numeral 310 shows actual measured values from the inhalation sensor 106 over a period of time when the inhalation is not performed. When the inhalation is not performed, ideal measured values from the inhalation sensor 106 over a period of time should be constant at a zero value, but the actual measured values 310 include variations from the zero value. These variations are caused by the vibration of air due to people talking or the like in the surrounding environment of the aerosol generating device 100 or the background noise generated by thermal disturbance or the like in the circuit. This background noise is further generated by change in the atmospheric pressure of the surrounding environment of the aerosol generating device 100 or the impact applied to the aerosol generating device 100.

Furthermore, when an electrostatic capacitance type MEMS (Micro Electro Mechanical Systems) sensor is used as the inhalation sensor 106, the output values from the sensor until the vibration of the electrode plate is convergent may also cause this background noise. The first threshold Thre1 may be set to a value at which some background noise can be picked up to perform preheating with good responsiveness. For example, in FIG. 3A, a part 311 of the measured values 310 somewhat exceeds the first threshold Thre1. That is, it may be expressed as:

$$\text{Thre1} - 0 \sim N_{pmax} \quad (1)$$

wherein $N_{pmax}$ represents a positive maximum value of the background noise over a period of time.

Reference numeral 320 shows the actual measured values including the background noise when the inhalation is performed by which the measured value of about the first threshold Thre1 is obtained. The first threshold Thre1 is originally a value for detecting the inhalation in such a level. The second threshold Thre2 may be set not to pick up the noise even when the inhalation in this level is performed. That is, it may be expressed as:

$$\text{Thre1} + N_{pmax} < \text{Thre2} \quad (2).$$

Considering now $$\text{Thre1} - 0 = N_{pmax} \quad (3)$$

as a special case of the expression (1), the expression (2) may be transformed as follows.

$$\text{Thre1} + \text{Thre1} - 0 < \text{Thre2} \quad \text{Thre1} < \text{Thre2} - \text{Thre1} \quad (4)$$

The expression (4) shows that a difference between the second threshold Thre2 and the first threshold Thre1 being larger than the first threshold Thre1 enables a situation where the preheating is to be performed without generating the aerosol to be clearly distinguished from a situation where the aerosol is to be generated, without determining the magnitude of the background noise. In other words, this means that erroneous recognition between the first threshold Thre1 and the second threshold Thre2 can be prevented, and when the power P1 and the power P2 are set to appropriate values, the generation of the aerosol can be started at a correct timing, the power P1 being a power supply amount when the measured value is larger than the first threshold Thre1 and smaller than or equal to the second threshold Thre2, and the power P2 being a power supply amount when the measured value is larger than the second threshold Thre2.

2-2-3 Power Supply Stop Condition

An example of the power supply stop condition in step S214 is a condition that the measured value from the inhalation sensor 106 falls below a third threshold. Thre3 which is equal to or larger than the second threshold Thre2. Such a relationship among the third threshold Thre3, the second threshold. Thre2 and the first threshold Thre1 will be described in detail with reference to FIGS. 3A and 3B again.

Figure 3A:
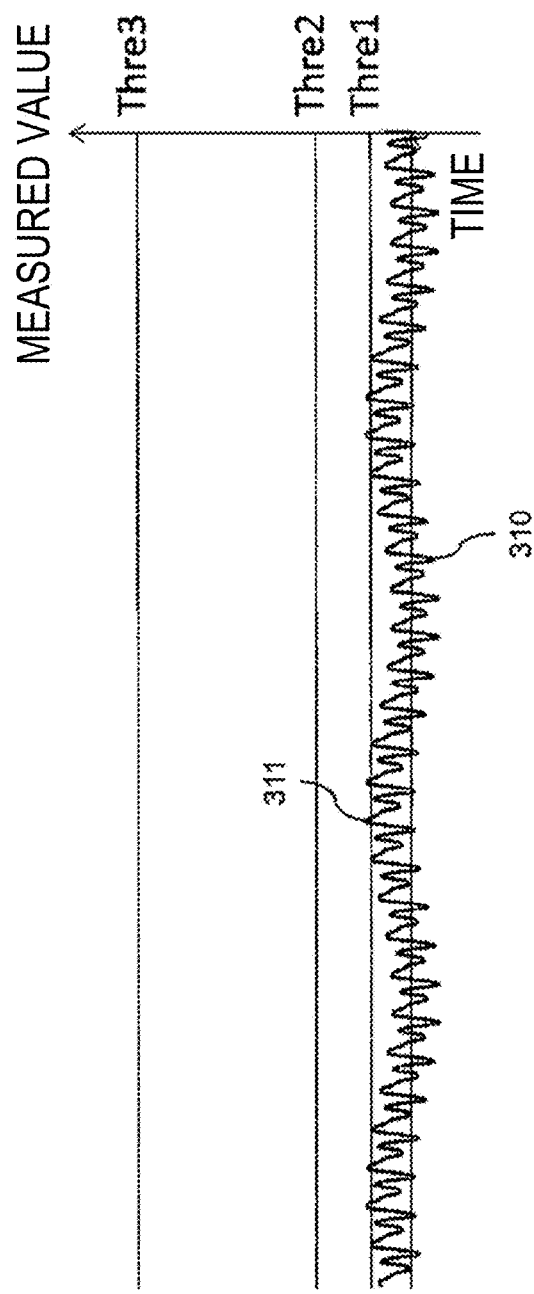
FIG. 3A is a graph showing a relationship among a first threshold Thre1, a second threshold Thre2, and a third threshold Thre3.
Figure 3B:
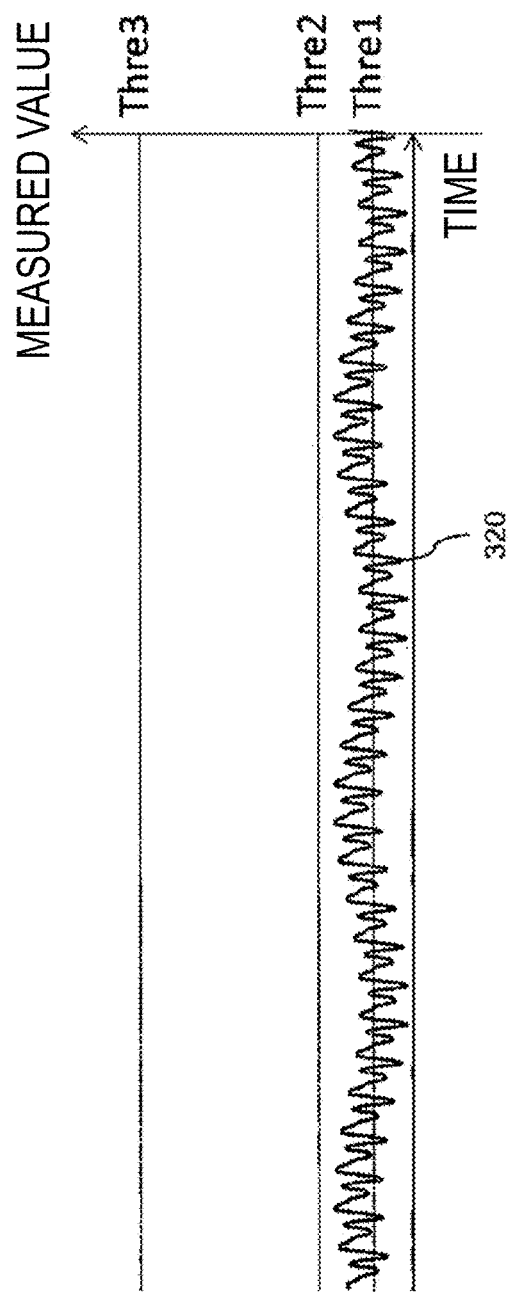
FIG. 3B is a graph showing a relationship among the first threshold Thre1, the second threshold Thre2, and the third threshold Thre3.

As shown in FIGS. 3A and 3B, the second threshold Thre2 may be set to be closer to the first threshold Thre1 than the third threshold Thre3. Setting the second threshold Thre2 in this manner enables the aerosol generation to be started earlier, so that supplying the power can be stopped earlier. The aerosol can be also generated with less of unnatural feeling to the inhalation of the user.

Unlike FIGS. 3A and 3B, the second threshold Thre2 may be set to be closer to the third threshold Thre3 than the first threshold Thre1 or to be equal to the third threshold Thre3. Setting the second threshold Thre2 in this manner makes it easier to avoid the forcible termination of the aerosol generation even when the power supply stop condition is a simple condition that the measured value is smaller than or equal to the third threshold Thre3, since the possibility that the measured value is smaller than or equal to the third threshold Thre3 when the process of step S214 is performed for the first time is reduced on an assumption that the measured value is gradually increased.

2-2-4 Power Source and Power

In step S206 and step S212, the power source is intended to at least include the battery 114 and the power controller 135. In this regard, the same is true for other exemplary operations shown below.

In step S206 and step S212, the power supplied to the heater may be constant over a period of time, or may change over a period of time so that the power supply amount per unit time is constant. In the present exemplary operations, it is intended that the values of the powers P1 and P2 each are a power supply amount (energy) per unit time. However, it is intended that the length of the unit time is any length including 1 s, and for example, the length of the unit time may be the length of one PWM cycle when the PWM control is used for supplying the power. Note that when the length of the unit time is not 1 s, the physical quantities of the powers P1 and P2 are not "(electric) powers," but are expressed as "powers" for the sake of convenience. In this respect, the same is true for other exemplary operations shown below.

Figure 4:
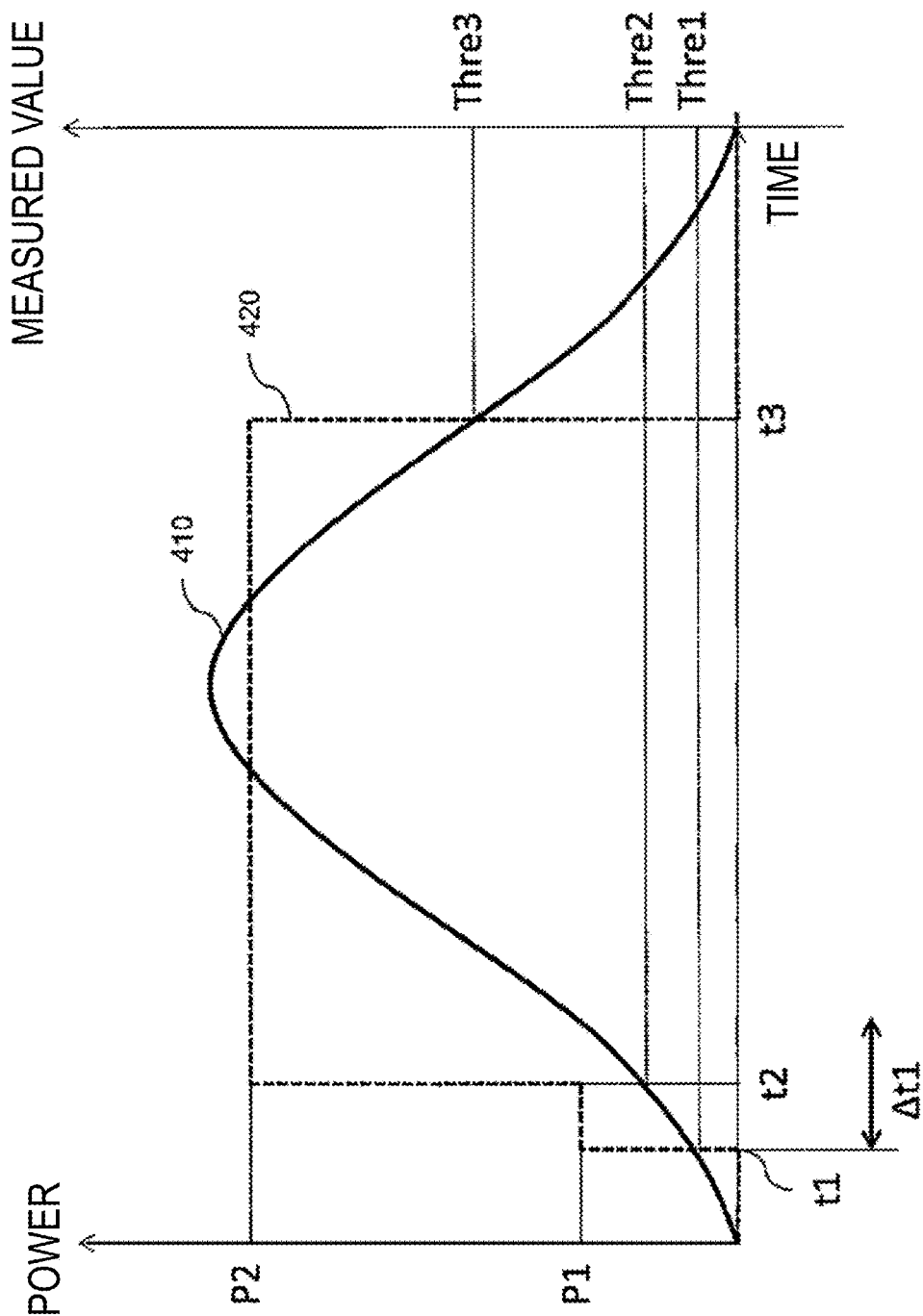
FIG. 4 is a graph showing changes in measured values 310 of an inhalation sensor 106 over a period of time, and changes in powers 320 supplied over a period of time.

The powers P1 and P2 will be described in detail with reference to FIG. 4. FIG. 4 is a graph showing changes in measured value 410 (solid line) of the inhalation sensor 106 over a period of time (hereinafter also referred to as a "puff profile" or a "profile of the measured values"), and changes in power 420 (dotted line) supplied to the heater of the atomizer 104 over a period of time. FIG. 4 shows that the supply of the power P1 is started at a time t1 when the measured value 410 exceeds the first threshold Thre1, the measured value 410 exceeds the second threshold Thre2 before a predetermined time Δt1 elapses after the supply of the power P1 is started, resulting that the supply of the power P2 is started at a time t2 when the measured value 410 exceeds the second threshold Thre2, and supplying the power is stopped at a time t3 when the measured value 410 falls below the third threshold Thre3. Note that the determination at the time t1 corresponds to the determination in step S202 in the flowchart of FIG. 2, the determination at the time t2 corresponds to the determination in step S210 in the flowchart of FIG. 2, the determination at the time 13 corresponds to the determination in step S214 in the flowchart of FIG. 2, and the predetermined time Δt1 corresponds to Δt1 in step S208 in the flowchart of FIG. 2.

It should be noted that the puff profile represented in FIG. 4 is a simplified example for purposes of illustration. The controller 130 can control the power supplied based on a puff profile based on the measured values obtained during a single cycle period such as in a single power supply cycle, a puff profile based on an average of the measured values obtained over periods of multiple cycles, a puff profile based on a regression analysis of the measured values obtained over periods of multiple cycles, or the like. Note that the "power supply cycle" includes the period from the start to the end of supplying the power, and may be the period from when the measured value exceeds zero or a predetermined minute value to when the measured value returns to zero or falls below the predetermined minute value, or the period in which a predetermined time is added to the beginning and/or the ending of such a period. The period from the left end to the right end of the time axis of the graph shown in FIG. 4 is an example of the "power supply cycle." In this regard, the same is true for other exemplary operations shown below.

The power P1 is a power supplied for the period during which the measured value 410 is larger than the first threshold Thre1 and is smaller than or equal to the second threshold Thre2. When the power P1 supplied for this period is used as preheating of the heater of the atomizer 104, the power P1 must satisfy the following expression.

$$J_{atomize}/\Delta t1 > P1/\Delta t_{unit} \quad (5)$$

wherein $J_{atomize}$ represents the minimum energy required to cause the atomization in the atomizer 104. Note that $J_{atomize}$ may be theoretically or experimentally obtained based on a composition of the aerosol source and a configuration of the heater of the atomizer 104. $\Delta t_{unit}$ represents a length of the unit time, and when the length of the unit time is 1 s, "/$\Delta t_{unit}$" may be omitted. Note that $J_{atomize}$ may not necessarily be a fixed value, and may be a variable varying depending on the conditions and the other variable. By way of example, the controller 130 may correct $J_{atomize}$ based on a remaining amount of the aerosol source.

The power P2 is a power supplied when the measured value 410 exceeds the second threshold Thre2, thereby causing the atomization in the atomizer 104. Accordingly, the power P2 is preferably a value as large as possible without adversely affecting the atomizer 104, for example, without causing failure of the heater due to overheating, and can satisfy at least the following condition.

$$P2 > P1 \quad (6)$$

When satisfying the expression (5), the power P1 can be made as large as possible, thereby reducing the predetermined time period Δt1. Accordingly, the power P1 satisfying zero value<P1<P2 may be set to be closer to P2 than the zero value.

2-2-5 Processing Derived from Flowchart 200

A series of steps included in the flowchart 200 show an example of the processing in which the power supply amount from the power source when the measured value from the inhalation sensor 106 is larger than the first threshold Thre1 and smaller than or equal to the second threshold Thre2 is at most predetermined value (power P1×predetermined time Δt1).

According to such processing, when the power supply amount from the power source when the measured value from the inhalation sensor 106 is larger than the first threshold Thre1 and smaller than or equal to the second threshold Thre2 is a first value, the first value necessarily becomes smaller than or equal to the predetermined value, and therefore the power supplied can be controlled so that the power supply amount when the measured value is larger than the second threshold Thre2 is larger than the first value. Accordingly, such processing leads to reduction in wasteful power consumption and wasteful consumption of the aerosol source even when the first threshold Thre1 is set at a value which is often unintentionally exceeded by the measured value due to the influence of background noise, for example.

The above-described predetermined value may be less than the power supply amount when the aerosol generation is started in the atomizer 104. The power supply amount as the first value does not cause the atomization in the atomizer 104, but the heater of the atomizer 104 is preheated using such a value. Preheating enables the intended aerosol generation to be started with good responsiveness without causing wasteful consumption of the aerosol source and without affecting the surroundings due to unintentional aerosol generation. From another viewpoint, at least one of the power for applying the power supply amount as the first value or the amount of power P1 per unit time and the predetermined time Δt1 may be set such that the first value is less than or equal to the power supply amount when the generation of the aerosol from the aerosol source is started. Note that the predetermined time Δt1 may be set between the predetermined upper limit and lower limit. Examples of the upper limit of the predetermined time Δt1 include 500 msec, 300 msec, and 100 msec. Examples of the lower limit of the predetermined time Δt1 include 10 msec and 30 msec.

A series of steps included in the flowchart 200 show an example of the processing in which supplying the power is stopped when the measured value does not exceed the second threshold Thre2 within the predetermined time Δt1 after the measured value exceeds the first threshold value Thre1 or the supply of the power P1 is started. According to such processing, the noise does not cause a situation in which the energization almost continues even when the first threshold Thre1 associated with the start of the energization is set to a sensitive value, which may cause picking up of noise, and therefore the amount of charges stored in the power source can be prevented from being reduced.

2-3 Variation of Flowchart 200

Furthermore, variation of the flowchart 200 will be described.

As described above, both of the pressure or flow sensor and an operation button can be used as the inhalation sensor 106. When the operation button is provided as the inhalation sensor 106, in step S202, the controller 130 may determine not whether the measured value exceeds the first threshold Thre1 but whether the operation button is pressed.

Step S206 may be performed before step S204, or step S204 and step S206 may be performed simultaneously (in parallel).

Another example of the power supply stop condition in step S214 is a condition that the measured value from the inhalation sensor 106 falls below the third threshold Thre3 after the power source supplies the power of a second value. The second value is a minimum power supply amount from the power source when the measured value exceeds the second threshold Thre2, and may be larger than the above-described first value which is the power supply amount before the measured value exceeds the second threshold Thre2. In this case, the power supply amount before the measured value exceeds the second threshold Thre2 is smaller than the second value.

Furthermore, the flowchart 200 may be modified so that step S204 is removed, and step S208 is modified to the step in which the controller 130 determines whether the total power supply amount at the moment of the step is smaller than or equal to the predetermined value. A series of steps included in the modified flowchart 200 show another example of the processing in which the power supply amount from the power source when the measured value of the inhalation sensor 106 is larger than the first threshold Thre1 and smaller than or equal to the second threshold Thre2 is at most predetermined value (power P1×predetermined time Δt1). It should be noted that the processing is not limited to the above-described two examples.

3 Second Exemplary Operations of Controller 130

Figure 5A:
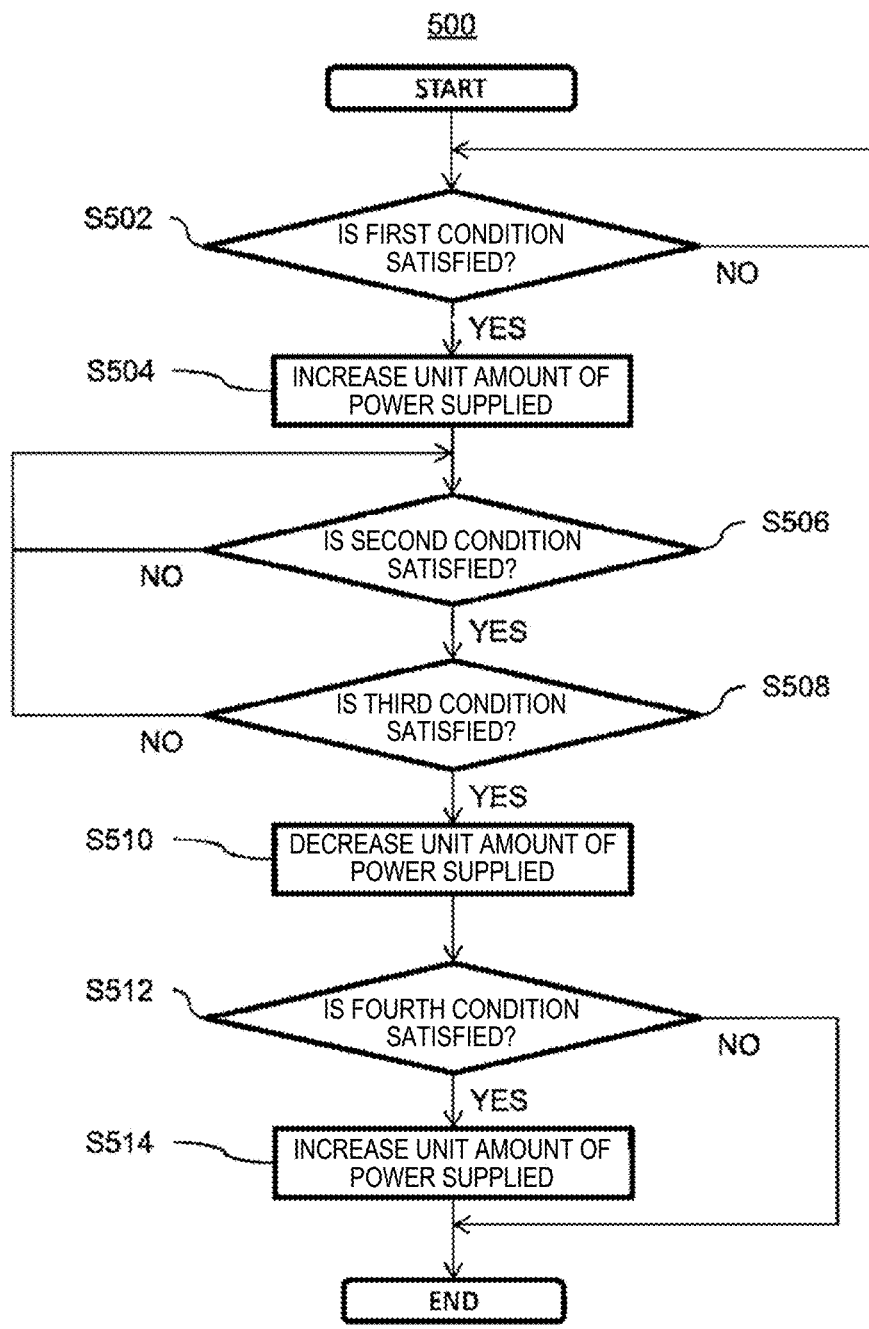
FIG. 5A is a flowchart 500 illustrating second exemplary operations of the controller 130.

FIG. 5A is a flowchart 500 illustrating second exemplary operations of the controller 130.

3-1 Outline of Flowchart 500

Firstly, the outline of the flowchart 500 will be described.

In step S502, the controller 130 determines whether a first condition is satisfied. If the first condition is satisfied, the process proceeds to step S504, and if no, the process returns to step S502. In step S504, the controller 130 controls to increase a value of power supplied (a power supply amount per unit time as described above. Hereinafter, referred to as a "unit amount of power supplied") to the heater of the atomizer 104.

In step S506, the controller 130 determines whether a second condition is satisfied. If the second condition is satisfied, the process proceeds to step S508, and if no, the process returns to step S506. In step S508, the controller 130 determines whether a third condition is satisfied. If the third condition is satisfied, the process proceeds to step S510, and if no, the process returns to step S506. In step S510, the controller 130 controls to decrease the unit amount of power supplied.

In step S512, the controller 130 determines whether a fourth condition is satisfied. If the fourth condition is satisfied, the process proceeds to step S514 in which the controller 130 controls to increase the unit amount of power supplied, and if no, the processing of the flowchart 500 is ended.

3-2 Detail of Flowchart 500

Next, the operations of the flowchart 500 will be described in detail.

3-2-1 First Condition

The first condition in step S502 may be a condition that the measured value from the inhalation sensor 106 exceeds the first threshold Thre1 or the second threshold Thre2.

3-2-2 Second Condition

The second condition in step S506 may be a condition that the measured value from the inhalation sensor 106 falls below the third threshold Thre3. Here, the third threshold Thre3 may be updated.

As a first example of the updating technique of the third threshold Thre3, the controller 130 can calculate and store the maximum value of the measured values every period from when supplying the power is started to when supplying the power is stopped or every power supply cycle, and update the third threshold Thre3 based on the plurality of maximum values calculated by the controller 130.

More specifically, the controller 130 can update the third threshold Thre3 based on the average $v_{max\_ave}$ which is derived from the plurality of maximum values calculated by the controller 130. An example of the simple average calculation is described below.

[Formula 1]

$$v_{max\_ave} = \frac{\sum_{i=1}^{N} v_{max}(i)}{N} \qquad (7)$$

Also, an example of the weighted average calculation is described below.

[Formula 2]

$$v_{max\_ave} = \frac{\sum_{i=1}^{N} \left(\frac{N-i+1}{N}\right)^{-1} \times v_{max}(i)}{\sum_{i=1}^{N} \left(\frac{N-i+1}{N}\right)^{-1}} \qquad (8)$$

wherein, in the expressions (7) and (8), N represents the number of periods in which the maximum value is calculated, and $v_{max}(i)$ represents the maximum value in the i-th period (the larger the value of i is, the newer the maximum value is). Such an average calculation is useful when the aerosol generating device 100 is used for a long period of time.

Particularly, according to the weighted average calculation, a greater weight can be assigned to the maximum value calculated in a more recent period from when supplying the power is started to when supplying the power thus started is stopped, to thereby accommodate changes in puff profiles when the aerosol generating device 100 is used for along period of time.

An example of an expression used to obtain a value to update the third threshold Thre3 is described below.

$$\text{Thre3} = v_{max\_ave} \times \alpha \qquad (9)$$

wherein, α is a value larger than zero and smaller than or equal to 1, and the third threshold Thre3 is preferably a value larger than the second threshold Thre2.

Figure 6A:
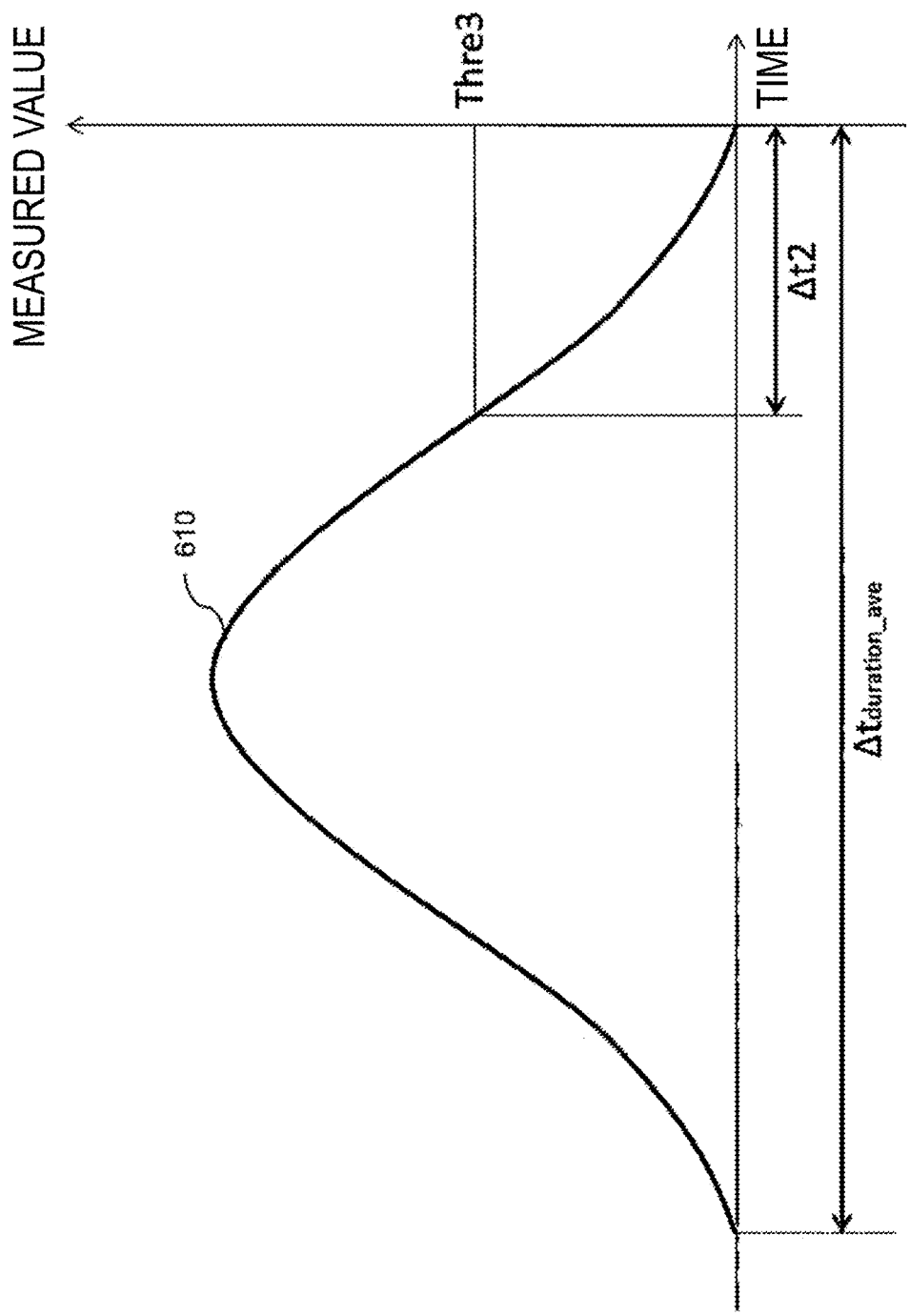
FIG. 6A is a graph for showing an example of an updating technique of the third threshold Thre3.

As a second example of the updating technique of the third threshold Thre3, the controller 130 can store changes in the measured values, i.e., a profile every period from when supplying the power is started to when supplying the power is stopped or every power supply cycle, and update the third threshold Thre3 based on the changes in the plurality of measurement values stored by the controller 130. Particularly, the third threshold Thre3 can be updated based on a value obtained by subtracting a predetermined value Δt2 from an average value $\Delta t_{duration\_ave}$ of the duration during which the measured value changes (for example, a length of the time from when the measured value exceeds zero or a predetermined minute value to when the measured value returns to zero or falls below the predetermined minute value). An example of an expression used to obtain a value to update the third threshold Thre3 is described below.

$$Thre3 = v(\Delta t_{duration\_ave} - \Delta t2)$$

wherein, referring to FIG. 6A, v(t) is a function that represents a puff profile 610, and $\Delta t_{duration\_ave}$ and Δt2 correspond to the times shown in FIG. 6A. It should be noted that the puff profile represented in FIG. 6A is intended to be based on the average of the measured values obtained in periods of multiple cycles, but is a simplified example for purposes of illustration.

Note that, in the present embodiment, a length of the time from when the measured value exceeds zero or a predetermined minute value to when the measured value returns to zero or falls below the predetermined minute value is used to determine the duration of the measured values. Alternatively, a length of the time until the measured value falls below zero or the predetermined minute value a plurality of times in succession may be used. In addition to these, the time derivative of the measured values may be used.

3-2-3 Comparison Between First Condition and Second Condition

When the thermal capacity of the wick 112 is large, the controller 130 preferably controls to advance the timing at which the unit amount of power supplied is increased and the timing at which the unit amount of power supplied is decreased, to generate the aerosol without unnatural feel to the inhalation of the user. That is, considering the ideal user profile in which the measured value is successively increased to reach the maximum value, and then is successively decreased to reach zero, the first threshold Thre1 or the second threshold Thre2 used in the first condition in step S502 of FIG. 5A is preferably a value smaller than the third threshold Thre3 used in the second condition in step S506 of FIG. 5A.

However, when the controller 130 increases or decreases the unit amount of power supplied only using the first condition and the second condition without using a third condition described later, the following problem may occurs, Since the first threshold Thre1 or the second threshold Thre2 used in the first condition is smaller than the third threshold Thre3 used in the second condition, the second condition is satisfied immediately after the first condition is satisfied, and therefore the unit amount of power supplied is decreased before the aerosol generation is performed by the increased unit amount of power supplied. More specifically, in step S506, it is determined whether the measured value which has exceeded the first threshold Thre1 or the second threshold Thre2 used in the first condition in step S502 falls below the third threshold Thre3. Considering that the measured values ideally successively change, and the control period and calculation speed of the controller 130, the measured value immediately after the measured value has exceeded the first threshold Thre1 or the second threshold Thre2 is highly likely to be smaller than the third threshold.

If a user profile changes ideally, the maximum value of the user profile has the same meaning as a maximal value. For example, the problem can be easily solved by calculating the changes in the measured values in the user profile changing in real time, and determining whether the measured value falls below the third threshold after the measured value reaches the maximum value (maximal value). However, since a real user profile has great differences among individuals, and the background noise is contained in the measured values shown in FIG. 3A and FIG. 3B, a plurality of maximal values are present. Therefore, the problem cannot be solved. In the present embodiment, a third condition is introduced to solve this problem.

3-2-4 Third Condition

The third condition in step S508 is a condition that is different from the first condition and the second condition. Accordingly, the third condition may be any condition that is not satisfied at the same tire as the first condition Such a third condition makes it possible to suppress such a situation where the unit amount of power supplied is decreased immediately after the first condition is satisfied and the unit amount of power supplied is increased. The third condition is any condition that can be satisfied after the second condition is satisfied (in other words, the second condition is satisfied prior to the third condition). According to such a third condition, the unit amount of power supplied is not decreased quickly even when the measured value from the inhalation sensor 106 is smaller than or equal to the third threshold Thre3, whereby the power can continues to be supplied.

3-2-4-1 Third Condition Based on Measured Values

The third condition may be based on the measured values from the inhalation sensor 106. Such a third condition makes it possible to avoid the situation where the unit amount of power supplied is decreased immediately after the unit amount of power supplied is increased, while taking into consideration the intensity of the inhalation.

More specifically, a first example of the third condition is a condition based on the tire derivative of the measured values. According to such a condition, by considering the changes in the intensity of the inhalation, it can be determined whether the unit amount of power supplied is decreased according to the feeling of the user. More specifically, the third condition may be a condition that the time derivative of the measured values is smaller than or equal to zero or the fourth threshold Thre4 which is smaller than zero. According to such a condition, the unit amount of power supplied is not decreased during a period in which the intensity of the inhalation continues to increase.

Note that, as described above, the background noise is contained into the measured values. Accordingly, strictly speaking, even when the intensity of the inhalation continues to increase, the time derivative of the measured values may be smaller than zero. The third condition may be a condition that the time derivative of the measured values is smaller than or equal to the fourth threshold Thre4 which is smaller than zero, whereby the unit amount of power supplied is not decreased even when the time derivative of the measured values becomes negative instantaneously. Note that the absolute value of the fourth threshold Thre4 being excessively large, results in an inability to recognize that the intensity of the inhalation continues to decrease and the end of the puff is approaching. Accordingly, the fourth threshold Thre4 may be set in consideration of the magnitude of the background noise to increase the accuracy.

When the magnitude of the background noise is considered, a fixed value taking account of the magnitude of the background noise when manufacturing the aerosol generating device 100 may be stored as the fourth threshold Thre4 in the memory 140. Alternatively, before implementing the flowchart 500, a change of the background noise over time continues to be stored in the memory 140 in a form of calibration, and the fourth threshold Thre4 may be set based on the maximum value or the average value which are derived from the change of the background noise.

In the present embodiment, the condition that the time derivative of the measured values is smaller than or equal to zero or the fourth threshold Thre4 which is smaller than zero is used as the third condition. Alternatively, the condition that the time derivative of the measured values is smaller than or equal to zero or the fourth threshold Thre4 which is smaller than zero is satisfied over a predetermined time in succession may be used as the third condition. This is because when the background noise changes as shown in FIG. 3A and FIG. 3B, the time derivative of the measured values is not continuously zero or smaller than or equal to the fourth threshold Thre4 which is smaller than zero, while the intensity of the inhalation continues to increase.

A second example of the third condition is a condition that the measured value falls below the second threshold Thre2 after exceeding a fifth threshold Thre5 which is equal to or larger than the second threshold Thre2. According to such a condition, the fifth threshold Thre5 is set to be close to an assumed maximum value, whereby the unit amount of power supplied can be controlled not to decrease until the measured value reaches at least the vicinity of the maximum value.

Here, the fifth threshold Thre5 can be updated.

As a first example of the updating technique of the fifth threshold Thre5, the controller 130 can calculate and store the maximum value of the measured values every period from when supplying the power is started to when supplying the power is stopped or every power supply cycle, and update the fifth threshold Thre5 based on the plurality of maximum values calculated by the controller 130. More specifically the controller 130 can update the fifth threshold Thre5 based on an average value of the plurality of maximum values calculated by the controller 130. The above-described average calculation in association with updating of the third threshold Thre3 can be used as the average calculation for obtaining the average value. A value to update the fifth threshold Thre5 can be obtained as follows.

$$\text{Thre5} = v_{max\_ave} - \Delta v1 \tag{10}$$

wherein $\Delta v1$ is a given value which is equal to or more than zero. By updating the fifth threshold Thre5, an appropriate magnitude value is set for the fifth threshold Thre5, thereby reducing the likelihood that the unit amount of power supplied decreases at inappropriate timing.

As a second example of the updating technique of the fifth threshold Thre5, the controller 130 can firstly update the third threshold Thre3, and then update the fifth threshold Thre5 to be equal to or larger than the updated third threshold Thre3. An example of an expression used to obtain a value to update the fifth threshold Thre5 is described below.

$$\text{Thre5} = \text{Thre3} + \Delta v2 \tag{11}$$

wherein $\Delta v2$ is a given value which is equal to or more than zero.

3-2-4-2 Third Condition Based on Dead Period

A dead period may be used as the third condition. That is, a third example of the third condition is a condition that a predetermined dead period $\Delta t_{dead}$ has elapsed since the first condition was satisfied. Such a third condition makes it possible to suppress such a situation where the unit amount of power supplied is decreased immediately after the unit amount of power supplied is increased because the unit amount of power supplied is not decreased until at least the dead period has elapsed.

The dead period $\Delta t_{dead}$ can be updated. For example, the controller 130 can calculate at least one of a first required time from when the first condition is satisfied to when the measured value reaches the maximum value and a second required time from when the first condition is satisfied to when the first condition is not satisfied every power supply cycle, and update the dead period $\Delta t_{dead}$ based on at least one of a plurality of first required times and a plurality of second required times.

More specifically, the controller 130 can update the dead period $\Delta t_{dead}$ based on at least one of an average value of the plurality of first required times and an average value of the plurality of second required times. An example of the simple average calculation is described below.

[Formula 3]

$$\Delta t_{ave} = \frac{\sum_{i=1}^{N} \Delta t(i)}{N} \tag{12}$$

Also, an example of the weighted average calculation is described below.

[Formula 4]

$$\Delta t_{ave} = \frac{\sum_{i=1}^{N} \left(\frac{N-i+1}{N}\right)^{-1} \times \Delta t(i)}{\sum_{i=1}^{N} \left(\frac{N-i+1}{N}\right)^{-1}} \tag{13}$$

Note that, in the expressions (12) and (13), N represents the number of periods in which the first required time or the second required time is calculated, and $\Delta t(i)$ represents the first required period or the second required period in the i-th period (the larger the value of i is, the newer the first required time or the second required time is). Such an average calculation is useful when the aerosol generating device 100 is used for a long period of time. Particularly, according to the weighted average calculation, a greater weight can be assigned to the first required period or the second required period which are calculated in a more recent period from when supplying the power is started to when supplying the power thus started is stopped, to thereby accommodate changes in puff profiles when the aerosol generating device 100 is used for a long period of time.

Three examples of an expression used to obtain a value to update the dead period $\Delta t_{dead}$ are described below.

[Formula 5]

$$\Delta t_{dead} = t_{max\_ave} - t_{over\_Thre1\_ave} + \Delta t3$$
$$\Delta t_{dead} = t_{under\_Thre1\_ave} - t_{over\_Thre1\_ave} - \Delta t4$$
$$\Delta t_{dead} = \frac{t_{max\_ave} + t_{over\_Thre1\_ave}}{2} - t_{over\_Thre1\_ave} \pm \Delta t5 \tag{14}$$

Figure 6B:
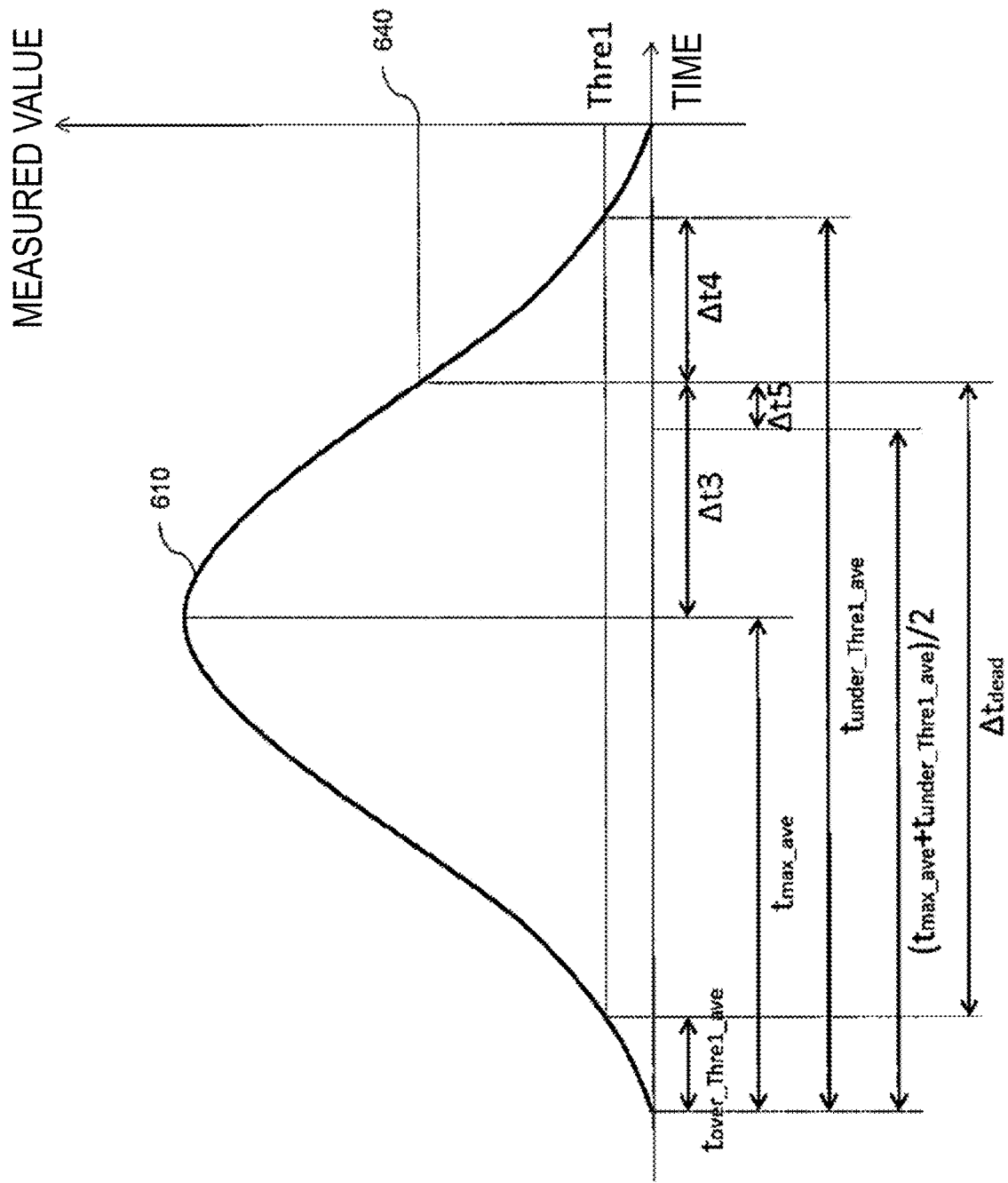
FIG. 6B is a graph for showing an example of an updating technique of a dead period.

Here, for the relationship of each variable in the above-described expressions, see FIG. 6B. Particularly, in the expressions $t_{over\_Thre1\_ave}$ represents an average value of the period from when the measured value exceeds zero or the predetermined minute value until the first condition is satisfied. Accordingly, in the expression, $t_{max\_ave} - t_{over\_Thre1\_ave}$ corresponds to the average value of the above-described first required times. In the expressions, $t_{under\_Thre1\_ave}$ represents an average value of the period from when the measured value exceeds zero or the predetermined minute value until the first condition is not satisfied. Accordingly, in the expression, $t_{under\_Thre1\_ave} - t_{over\_Thre1\_ave}$ corresponds to the average value of the above-described second required times. The magnitudes of $\Delta t3$, $\Delta t4$, and $\Delta t5$ are given values that are equal to or more than zero, and are preferably set so that a value indicated by reference numeral 640 in FIG. 6B becomes the third threshold Thre3. By updating the dead period $\Delta t_{dead}$, an appropriate magnitude value is set for the dead period $\Delta t_{dead}$, thereby reducing the likelihood that the unit amount of power supplied decreases at unexpected timing.

3-2-4-3 Other Third Condition

A fourth example of the third condition is a condition that at the time of determining the third condition, a predetermined time or more has elapsed since the measured value output until the third condition is determined became maximum.

3-2-4-4 Selection of Third Condition

Figure 7:
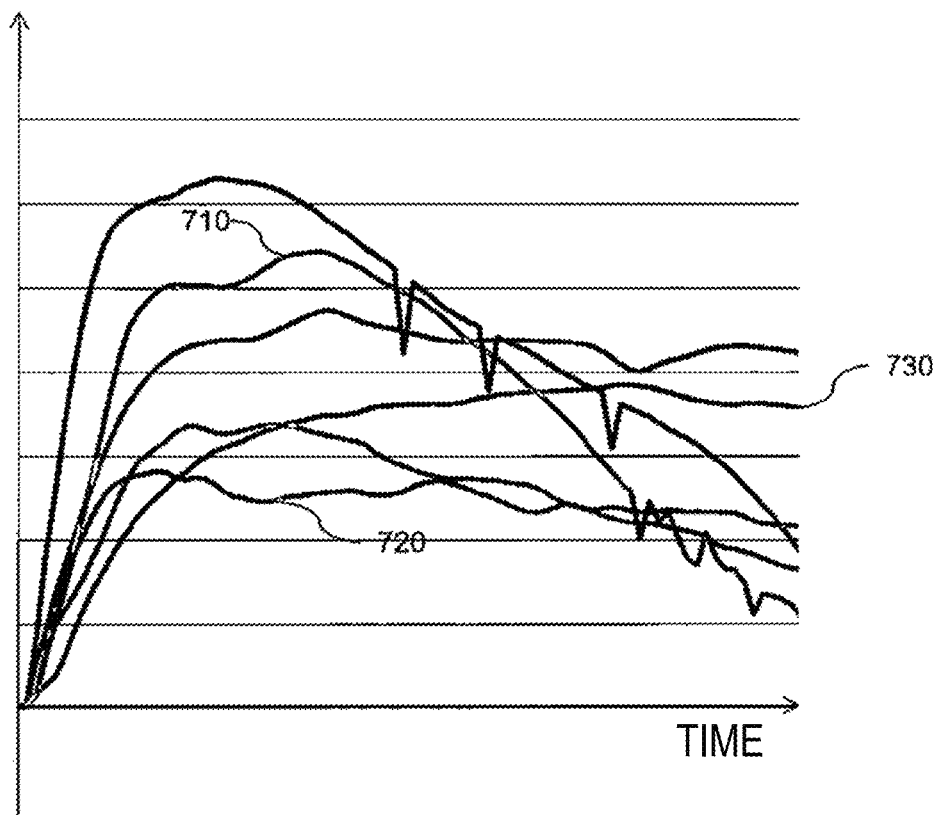
FIG. 7 is a graph showing various puff profiles.

The third condition can be selected from a plurality of third conditions. FIG. 7 is a graph showing various puff profiles. As can be seen from FIG. 7, suitable third conditions are different according to the puff profile. For example, since the puff profile indicated by reference numeral 710 has a maximal value before reaching the maximum value, in other words, the time derivative of the measured values becomes a negative value before the profile reaches the maximum value, the third condition using a derivative value (first example) is difficult to use. Since the puff profile indicated by reference numeral 720 generally has small measured values, the third condition using a plurality of thresholds (second example) is difficult to provide a significant difference among the measured values with respect to a plurality of thresholds, and is difficult to use. Furthermore, since the puff profile indicated by 730 requires a long period until the profile reaches the maximum value, the third condition using a dead period (third example) is difficult to use. Accordingly, the controller 130 can implement the selection mode in which the third condition is selectable from a third condition group including a plurality of third conditions. Particularly, the controller 130 can store the measured values from the inhalation sensor 106, and select the third condition from the third condition group based on the stored measured values, for example, the puff profile based on the stored measured values.

Figure 8:
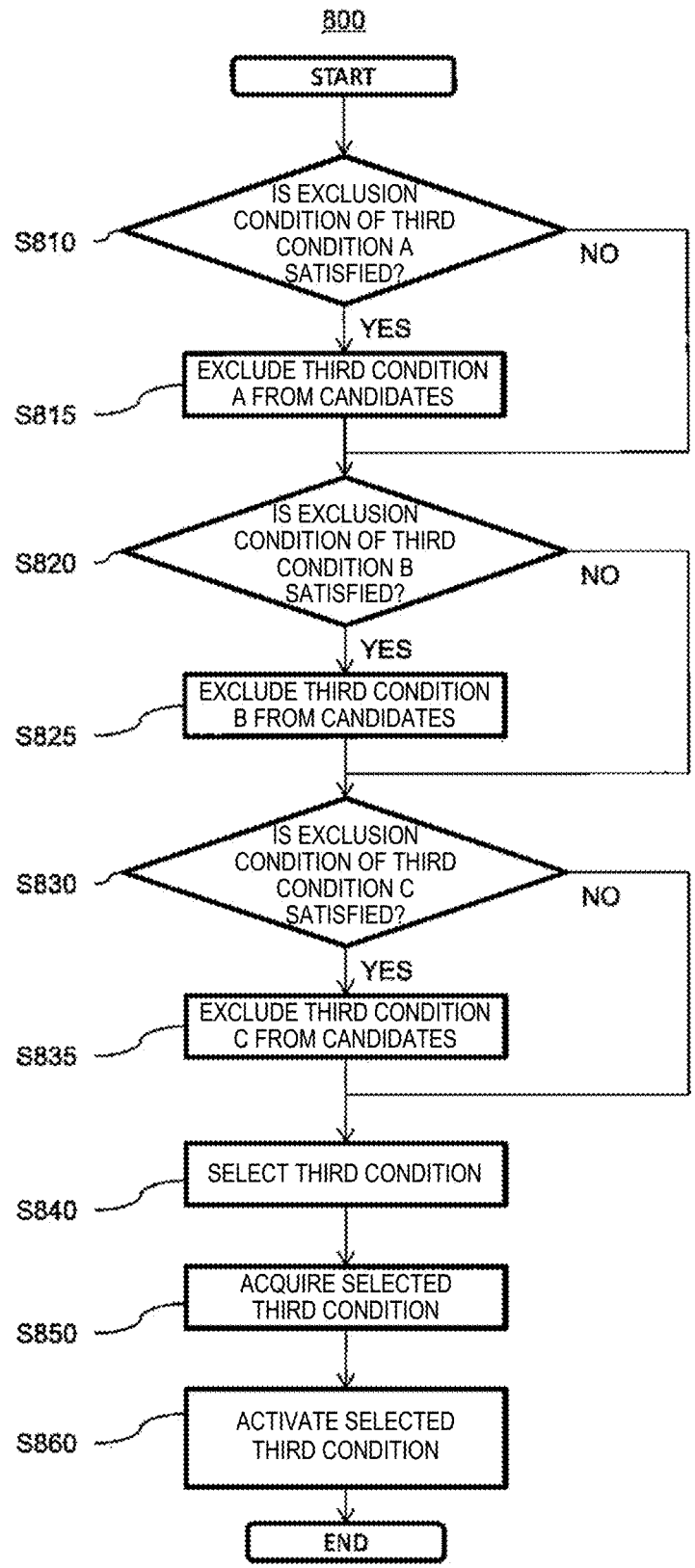
FIG. 8 is a flowchart 800 illustrating exemplary operations for selecting a third condition from a third condition group.

FIG. 8 is a flowchart illustrating an exemplary method 800 of selecting the third condition from the third condition group. Note that in FIG. 8, the number of third conditions included in the third condition group is assumed to be three of the third conditions A, B, and C, but the third condition group may include any number of third conditions that is greater than one.

In step S810, the controller 130 determines whether an exclusion condition of the third condition A is satisfied. The exclusion condition of the third condition A may be a condition based on the time derivative of the stored measured values, for example, that the measured values has the maximal value. When the exclusion condition of the third condition A is satisfied, the process proceeds to step S815, the third condition A is excluded from the candidates in step S815, and the process further proceeds to step S820. When the exclusion condition of the third condition A is not satisfied in step S810, the process proceeds to step S820, and therefore, in this case, the third condition A is not excluded from the candidates.

Steps S820 and S830 are steps corresponding to step S810, in which determinations are made concerning the third conditions B and C, respectively, the third conditions B and C being different from the third condition A. Here, the exclusion condition of the third condition B may be a condition based on the maximum value of the measured values, for example, that the measured values are generally small. The exclusion condition of the third condition C may be a condition based on the duration during which the measured value changes, for example, a long period is required until the measured value reaches the maximum value. Steps S825 and S835 are steps corresponding to step S815, in which the third conditions B and C are excluded from the candidates, respectively, the third conditions B and C being different from the third condition A.

In step S840, the controller 130 selects the third condition from the third conditions remaining as candidates. Note that when a plurality of candidates remain, the controller 130 can select one third condition from the remaining candidates. If no candidate remains, the controller 130 may select any third condition included in the third condition group. Possible examples of a method in which the controller 130 selects one or more third conditions from the plurality of third conditions include random selection, selection according to a priority order set in advance, user selection, and the like. Note that the aerosol generating device 100 includes input means (not illustrated) for receiving the user selection. The aerosol generating device 100 may include communication means (not illustrated) for connecting to a computer such as a smartphone through Wi-Fi, Bluetooth, or the like, to receive the user selection from the connected computer.

In step S850, the controller 130 acquires the selected third condition Acquiring the selected third condition includes acquiring the program according to an algorithm to determine such a condition. One or more third conditions which may be acquired from the third condition group may be stored in the memory 140 in advance, may be acquired from the outside, for example, the above-described computer such as a smartphone, or may be downloaded from the internet through the above-described communication means. When the third condition is acquired from the outside or from the internet, advantages can be obtained in that it is not necessary to store all of the third conditions included in the third condition group in the memory 140, thereby enabling free space of the memory 140 to be secured for other uses, it is not necessary to mount a high capacity memory 140, whereby the costs of the aerosol generating device 100 can be reduced, and it is not necessary to mount a large memory 140, whereby the aerosol generating device 100 can be miniaturized.

In step S860, the controller 130 configures itself to determine whether the selected third condition is satisfied.

3-2-5 Fourth Condition

The fourth condition in step S512 is a condition that the time derivative of the measured values from the inhalation sensor 106 exceeds zero within a predetermined return period from when the second condition and the third condition are satisfied. According to such a fourth condition, when the unit amount of power supplied is decreased due to the noise or a slight reduction in the inhalation intensity, the unit amount of power supplied can be rapidly increased, thereby improving the usability of the aerosol generating device 100.

3-2-6 Increase in Unit Amount of Power Supplied

In step S504, the increase in the unit amount of power supplied may be an increase from zero value to the unit amount of power supplied having a magnitude. This increase may be gradual, and for example, the unit amount of power supplied may be gradually increased from zero value to a first unit amount of power supplied, and then from the first unit amount of power supplied to a second unit amount of power supplied which is larger than the first unit amount of power supplied.

The increase in the unit amount of power supplied in step S514 may be an increase from zero value to the unit amount of power supplied having a magnitude which is increased in step S504.

3-2-7 Decrease in Unit Amount of Power Supplied

In step S510, the decrease in the unit amount of power supplied may be a decrease to zero value from the unit amount of power supplied having a magnitude.

3-3 Variation of Flowchart 500

Furthermore, variation of the flowchart 500 will be described.

Step S508 may be performed before step S506, or step S506 and step S508 may be performed simultaneously (in parallel).

Step S508 may be modified so that when the third condition is not satisfied within a predetermined determination period from when the first condition is satisfied, the process proceeds to step S510. This makes it possible to decrease the unit amount of power supplied even when the third condition is not satisfied, to thereby avoid the situation where the energization is not stopped.

Figure 5B:
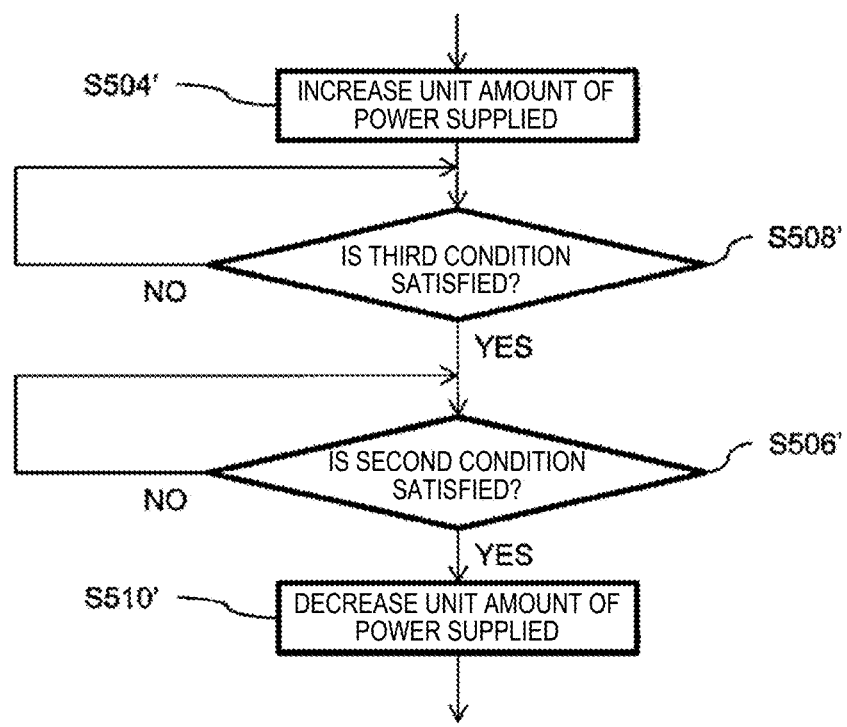
FIG. 5B is a part of a flowchart for illustrating a variation of the flowchart 500.

Steps S504 to S510 may be replaced with steps S504' to S510' illustrated in FIG. 5B, respectively. That is, the controller 130 may increase the unit amount of power supplied in step S504', and then determine, in step S508', whether the third condition is satisfied. If the third condition is satisfied, the process proceeds to step S506', and if no, the process returns to step S508'. Furthermore, the controller 130 determines, in step S506', whether the second condition is satisfied. If the second condition is satisfied, the process may proceed to step S510' to decrease the unit amount of power supplied, and if no, the process may return to step S506'. According to the variation illustrated in FIG. 5B, the controller 130 controls to decrease the unit amount of power supplied when the second condition is satisfied after the third condition is satisfied, the third condition being different from the first condition and the second condition.

4 Third Exemplary Operations of Controller 130

Figure 9:
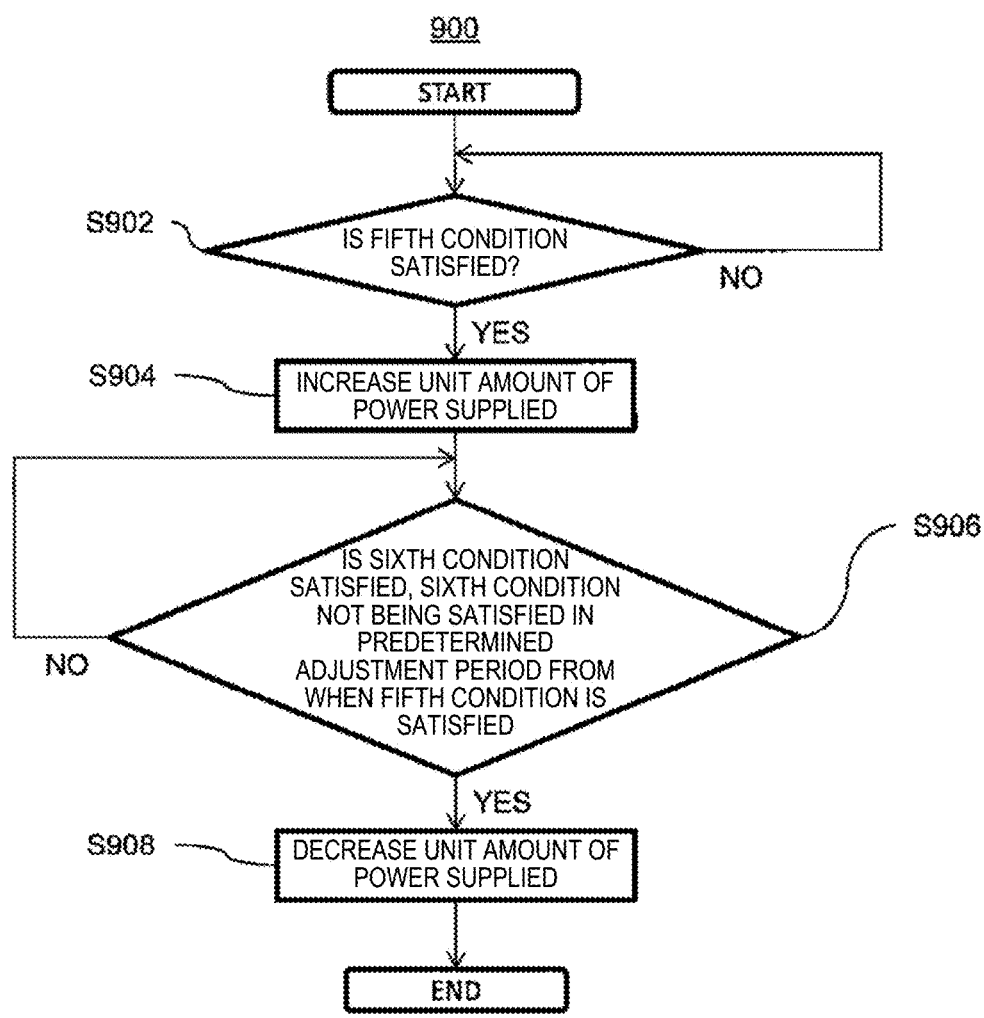
FIG. 9 is a flowchart 900 illustrating third exemplary operations of the controller 130.

FIG. 9 is a flowchart 900 illustrating third exemplary operations of the controller 130.

4-1 Outline of Flowchart 900

Firstly, the outline of the flowchart 900 will be described.

In step S902, the controller 130 determines whether a fifth condition is satisfied. If the fifth condition is satisfied, the process proceeds to step S904, and if no, the process returns to step S902. In step S9041 the controller 130 controls to increase the unit amount of power supplied.

In step S906, the controller 130 determines whether a sixth condition is satisfied, the sixth condition not being satisfied in a predetermined adjustment period from when the fifth condition is satisfied. If the sixth condition is satisfied, the process proceeds to step S908, and if no, the process returns to step S906. In step S908, the controller 130 controls to decrease the unit amount of power supplied.

4-2 Detail of Flowchart 900

Next, the operations of the flowchart 900 will be described in detail.

An example of the fifth condition in step S902 corresponds to the above-described first condition, and an example of the sixth condition in step S906 corresponds to the condition based on the dead period which has been described above with reference to the third condition. The predetermined adjustment period in step S906 is preferably equal to or longer than a control period (one step is performed for each one control period) of the controller 130. According to such a sixth condition, the condition for decreasing the unit amount of power supplied is satisfied immediately after the condition for increasing the unit amount of power supplied is satisfied, which makes it possible to avoid the situation where power cannot be substantially supplied indefinitely.

Steps S904 and S908 correspond to steps S504 and S510 of the flowchart 500, respectively.

5 Fourth Exemplary Operations of Controller 130

Figure 10:
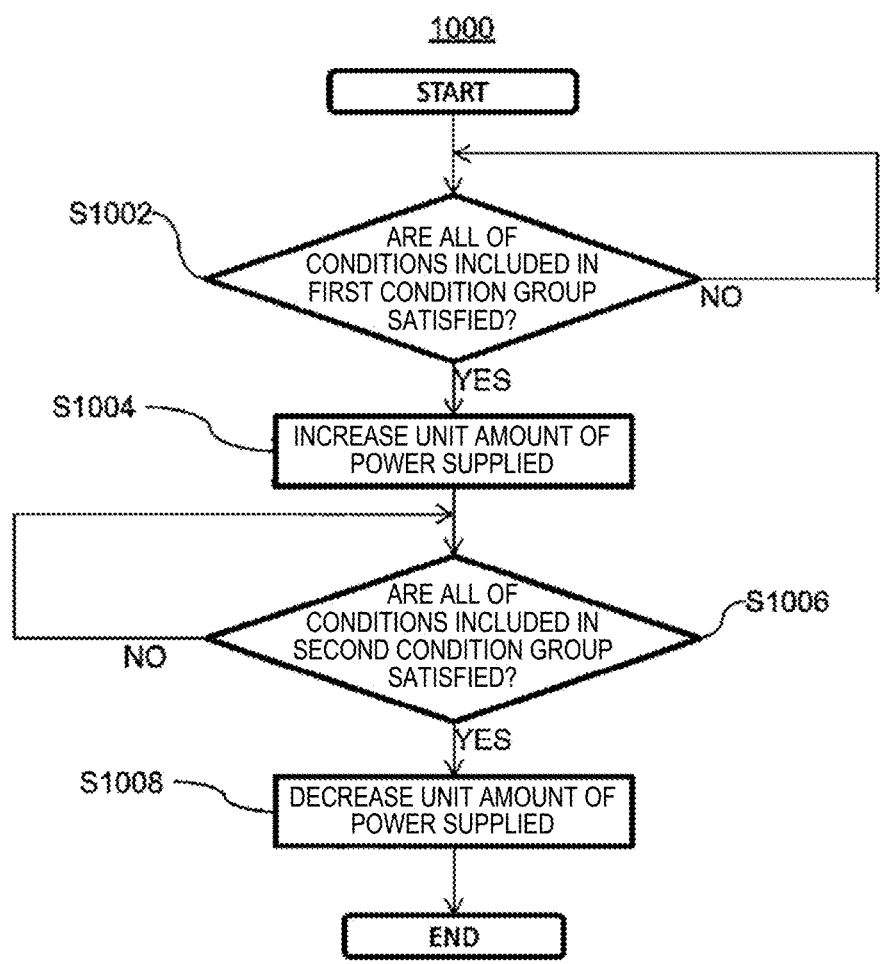
FIG. 10 is a flowchart 1000 illustrating fourth exemplary operations of the controller 130.

FIG. 10 is a flowchart 1000 illustrating fourth exemplary operations of the controller 130.

5-1 Outline of Flowchart 1000

Firstly, the outline of the flowchart 1000 will be described.

In step S1002, the controller 130 determines whether all of the one or more conditions included in the first condition group are satisfied. If all of the one or more conditions are satisfied, the process proceeds to step S1004, and if no, the process returns to step S1002. In step S10041 the controller 130 controls to increase the unit amount of power supplied.

In step S1006, the controller 130 determines whether all of the one or more conditions included in the second condition group are satisfied. If all of the one or more conditions are satisfied, the process proceeds to step S1008, and if no, the process returns to step S1006. In step S1008, the controller 130 controls to decrease the unit amount of power supplied.

5-2 Detail of Flowchart 1000

Next, the operations of the flowchart 1000 will be described in detail.

The number of conditions included in the first condition group can be smaller than the number of conditions included in the second condition group. This makes it more difficult to satisfy the conditions for decreasing the unit amount of power supplied than the conditions for increasing the unit amount of power supplied, whereby the unit amount of power supplied does not decrease easily.

More specifically, each of the first condition group and the second condition group may include at least one condition involving a common variable. This makes it possible to guarantee the certainty of increase and decrease in the unit amount of power supplied. For example, the common variables can be based on the measured values of the inhalation sensor 106, which makes it possible to control the supplied power with the user's intention reflected thereon. The condition involving a common variable may be a condition that an absolute value of the common variable is equal to or larger than a threshold, larger than a threshold, smaller than or equal to a threshold, or smaller than a threshold, and a threshold in the condition involving the common variable included in the first condition group may be different from a threshold in the condition involving the common variable included in the second condition group. At this time, the former threshold may be smaller than the latter threshold. This makes it possible to advance the timing from the increase of the unit amount of power supplied to the decrease of the unit amount of power supplied.

Note that examples of one or more conditions included in the first condition group are the above-described first conditions, and examples of one or more conditions included in the second condition group are the above-described second conditions and third conditions.

Steps S1004 and S1008 correspond to steps S504 and S510 of the flowchart 500, respectively. One or more conditions included in the first condition group are not limited only to the above-described first conditions, and other conditions may be used instead of or in addition to the first conditions. Similarly, one or more conditions included in the second condition group are not limited to the above-described second conditions and third conditions, and other conditions may be used instead of or in addition to these conditions.

6 Fifth Exemplary Operations of Controller 130

Figure 11:
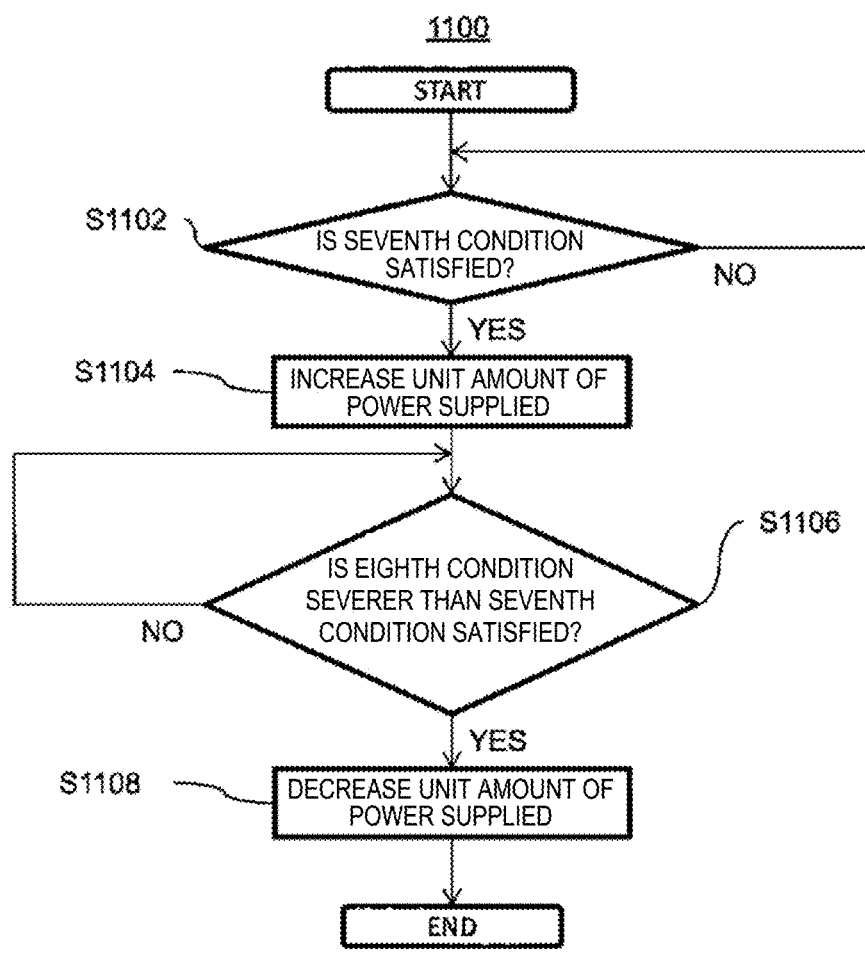
FIG. 11 is a flowchart 1100 illustrating fifth exemplary operations of the controller 130.

FIG. 11 is a flowchart 1100 illustrating fifth exemplary operations of the controller 130.

6-1 Outline of Flowchart 1100

Firstly, the outline of the flowchart 1100 will be described.

In step S1102, the controller 130 determines whether a seventh condition is satisfied. If the seventh condition is satisfied, the process proceeds to step S11041 and if no, the process returns to step S1102. In step S1104, the controller 130 controls to increase the unit amount of power supplied.

In step S1106, the controller 130 determines whether an eighth condition severer than the seventh condition is satisfied. If the eighth condition is satisfied, the process proceeds to step S1108, and if no, the process returns to step S1106. In step S1108, the controller 130 controls to decrease the unit amount of power supplied.

6-2 Detail of Flowchart 1100

The seventh condition in step S1102 may be a condition that is a necessary condition but not a sufficient condition of the eighth condition in step S1106. From another viewpoint, an example of the seventh condition may be the above-described first condition, and an example of the eighth condition may be a combination of the above-described second condition and third condition. To satisfy such an eighth condition, it is necessary to satisfy a complex condition comprising the combination of the second condition and the third condition. This makes it more difficult to satisfy the conditions for decreasing the unit amount of power supplied than the conditions for increasing the unit amount of power supplied, whereby the unit amount of power supplied does not decrease easily. The difference in the degree of severity between the seventh condition and the eighth condition should not be construed as being limited to the above description. For example, when the possibility that the eighth condition is satisfied is lower than the possibility that the seventh condition is satisfied, it can be said that the eighth condition is severer than the seventh condition. For example, when the eighth condition is not simultaneously satisfied even when the seventh condition is satisfied, it can be said that the eighth condition is severer than the seventh condition.

Steps S1104 and S1108 correspond to steps S504 and S510 of the flowchart 500, respectively.

7 Sixth Exemplary Operations of Controller 130

Figure 12:
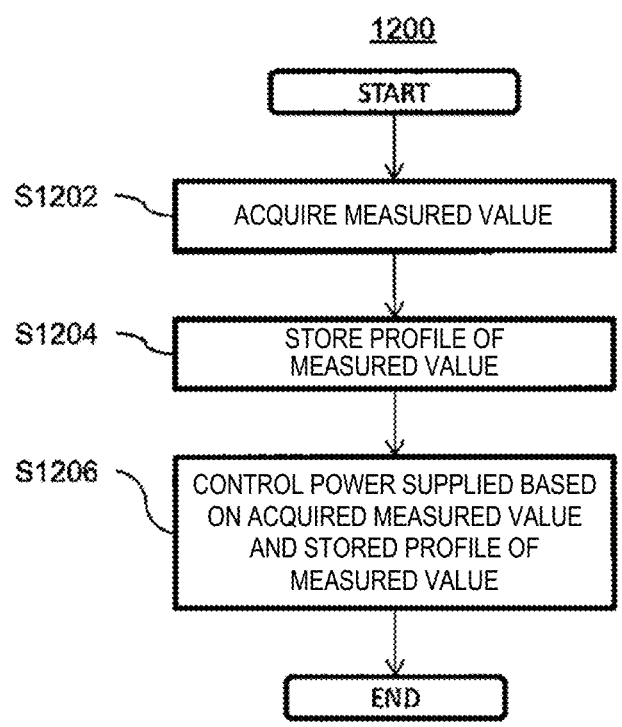
FIG. 12 is a flowchart 1200 illustrating sixth exemplary operations of the controller 130.

FIG. 12 is a flowchart 1200 illustrating sixth exemplary operations of the controller 130.

7-1 Outline of Flowchart 1200

Firstly, the outline of the flowchart 1200 will be described.

In step S1202, the controller 130 acquires the measured values of the inhalation sensor 106 which are measured values representing first physical quantities for controlling the power supplied. In step S1204, the controller 130 stores changes in the measured values representing the first physical quantities, i.e., the profiles. In step S1206, the controller 130 controls the supplied power by controlling second physical quantities which are different from the first physical quantities, based on the acquired measured values representing the first physical quantities and at least part of the stored profiles of the measured values representing the first physical quantities. Examples of the second physical quantities are current values associated with power supplied, voltage values, current values, and the like.

7-2 Detail of Flowchart 1200

Next, the operations of the flowchart 1200 will be described in detail.

7-2-1 Storing Profile of Measurement Values

Examples of storing the profiles of the measured values representing the first physical quantities for controlling the power supplied in step S1204 include storing, in the memory 140, both of the measured values representing the first physical quantities acquired in step S1202 and times when the measured values representing the first physical quantities are acquired. It should be noted that step S1202 is performed at least more than once. The controller 130 can store the profile of the measured values representing the first physical quantities every power supply cycle including a period from when supplying the power is started to when supplying the power is stopped. That is, the controller 130 can store the profile of the measured values corresponding to the power supply cycle.

7-2-2 Power Supply Control Based on Profile of Stored Measured Values

The controller 130 can determine a first profile and/or a second profile, the first profile being a profile of the measured values representing the first physical quantities for controlling the power supplied, the profile corresponding to one power supply cycle of a plurality of past power supply cycles each including a period from when supplying the power is started to when supplying the power is stopped, and the second profile being a profile of the measured values representing average first physical quantities derived from a plurality of first profiles. The controller 130 can control at least one of a stop and continuity of supplying the power based on at least one of the first profile and the second profile.

7-2-3 Example of Power Supply Control from First Viewpoint

The controller 130 can determine the first required time required from the start to the end of changes in the measured values representing the first physical quantities for controlling the power supplied, based on at least one of the first profile and the second profile. The changes in the measured values representing the first physical quantities may be started when the measured value representing the first physical quantity exceeds zero or the predetermined minute value. The changes in the measured values representing the first physical quantities may be ended when the measured value representing the first physical quantity falls to zero or below the predetermined minute value after the changes in the measured values representing the first physical quantities are started. The controller 130 can control the power supplied so that supplying the power is stopped at a timing earlier than elapse of the first required time. In other words, the controller 130 can control the power supplied so that the power continues to be supplied for a shorter time than the first required time.

Alternatively, the controller 130 can determine the second required time required from the start of changes in the measured values representing the first physical quantities until the measured value reaches the maximum value, based on at least one of the first profile and the second profile. The controller 130 can control the power supplied so that supplying the power is stopped at a timing later than elapse of the second required time. In other words, the controller 130 can control the power supplied so that the power continues to be supplied for a longer time than the second required time.

Note that the controller may determine both of the first required time and the second required time. In this case, the controller 130 can control the power supplied so that the supplying power is stopped at a timing earlier than elapse of the first required time and a timing later than elapse of the second required time. In other words, the controller 130 can control the power supplied so that the power continues to be supplied for a shorter time than the first required time and for a longer time than the second required time.

7-2-4 Example of Power Supply Control from Second Viewpoint

The controller 130 may be configured to be capable of executing a plurality of algorithms for setting the timing when supplying the power is stopped or a period of time in which the power continues to be supplied based on plurality of kinds of feature points in the first profile or the second profile. Regarding a first feature point which is one kind of the plurality of kinds of feature points, a plurality of first feature points can be derived from a plurality of first profiles or a plurality of second profiles, whereby the controller 130 can execute one of a first algorithm based on the first feature points based on deviations among the plurality of feature points and a second algorithm based on a second feature point which is the other kind of the plurality of kinds of feature points. The deviations among the feature points may be deviations among the measured values representing the first physical quantities at the feature points, or deviations among the times of the feature points, i.e., measurement times of the measured values at the feature points with reference to any time, e.g., the time when the changes in the measured values representing the first physical quantities are started.

More specifically, the controller 130 can execute the first algorithm when values based on the deviations among the plurality of first feature points are smaller than or equal to a threshold. The values based on a plurality of deviations include an average value (mean deviation) of absolute values of the plurality of deviations, an average value of the square of the plurality of deviations (variance), and a square root (standard deviation) of the average value of the square of the plurality of deviations.

An example of one kind of feature point of a plurality of kinds of feature points is a point at which the first profile or the second profile is ended, that is, an end point. Another example of one kind of feature point of the plurality of kinds of feature points is a point at which the measured value representing the first physical quantity in the first profile or the second profile becomes maximum. The number of possible values of the measurement time of the measured value (maximum value) representing the first physical quantity at the latter kind of feature point would be larger than that of possible values of the measurement time of the measured value (zero or minute value) representing the first physical quantity at the former kind of feature point. The measurement time of the measured value representing the physical quantity at the latter kind of feature point is later than the measurement time of the measured value representing the first physical quantity at the former kind of feature point. Furthermore, the former kind of feature point would be after the latter kind of feature point in the time series.

Note that when an end point of the first profile or the second profile is used for the first feature point, and a point at which the measured value representing the first physical quantity in the first profile or the second profile becomes maximum is used for the second feature point, the measured value of the first feature point becomes smaller than the measured value of the second feature point. In terms of the properties of each of the first and second feature points, in the first profile and the second profile, the number of points which may correspond to the first feature point (points at which the measured value is smaller than or equal to zero or the minute value in the power supply cycle. A plurality of points are normally present.) is normally larger than that of points which may correspond to the second feature point (points at which the measured value becomes maximum in the power supply cycle. Only one point is present in many cases, but a plurality of points are present if maximum measured values are successively obtained.). In other words, as compared with the second feature point, it can be said to be difficult to determine the first feature point in the first profile and the second profile.

7-2-5 Example of Power Supply Control from Third Viewpoint

The controller 130 can acquire the current timing when supplying the power is stopped. The current timing when supplying the power is stopped may be the timing, which was derived from the first profile or the second profile or stored in the memory 140 in the past, when supplying the power is stopped. The controller 130 may control the supplied power based on the current timing when supplying the power is stopped, when a difference between the timing when supplying the power is stopped which is derived from the first profile or the second profile and the current timing when supplying the power is stopped is smaller than or equal to a threshold. If the controller 130 strictly uses the timing when supplying the power is stopped derived from the first profile or the second profile even when the difference between the timing when supplying the power is stopped derived from the first profile or the second profile and the current timing when supplying the power is stopped is minimal, the timing when supplying the power is stopped is frequently changed, which causes complicated control, and thus causes an unnatural feeling of the user.

In other words, the controller 130 can acquire a current period of time in which the power continues to be supplied. The current period of time in which the power continues to be supplied may be a period of time, which was derived from the first profile or the second profile or stored in the memory 140 in the past, in which the power continues to be supplied. The controller 130 may control the supplied power based on the current period of time in which the power continues to be supplied, when a difference between the period of time, which is derived from the first profile or the second profile, in which the power continues to be supplied and the current period of time in which the power continues to be supplied is smaller than or equal to a threshold. If the controller 130 strictly uses the period of time, which is derived from the first profile or the second profile, in which the power continues to be supplied even when the difference between the period of time, which is derived from the first profile or the second profile, in which the power continues to be supplied and the current period of time in which the power continues to be supplied is minimal, the period of time in which the power continues to be supplied is frequently changed, which causes complicated control, and thus causes an unnatural feeling of the user.

Figure 13:
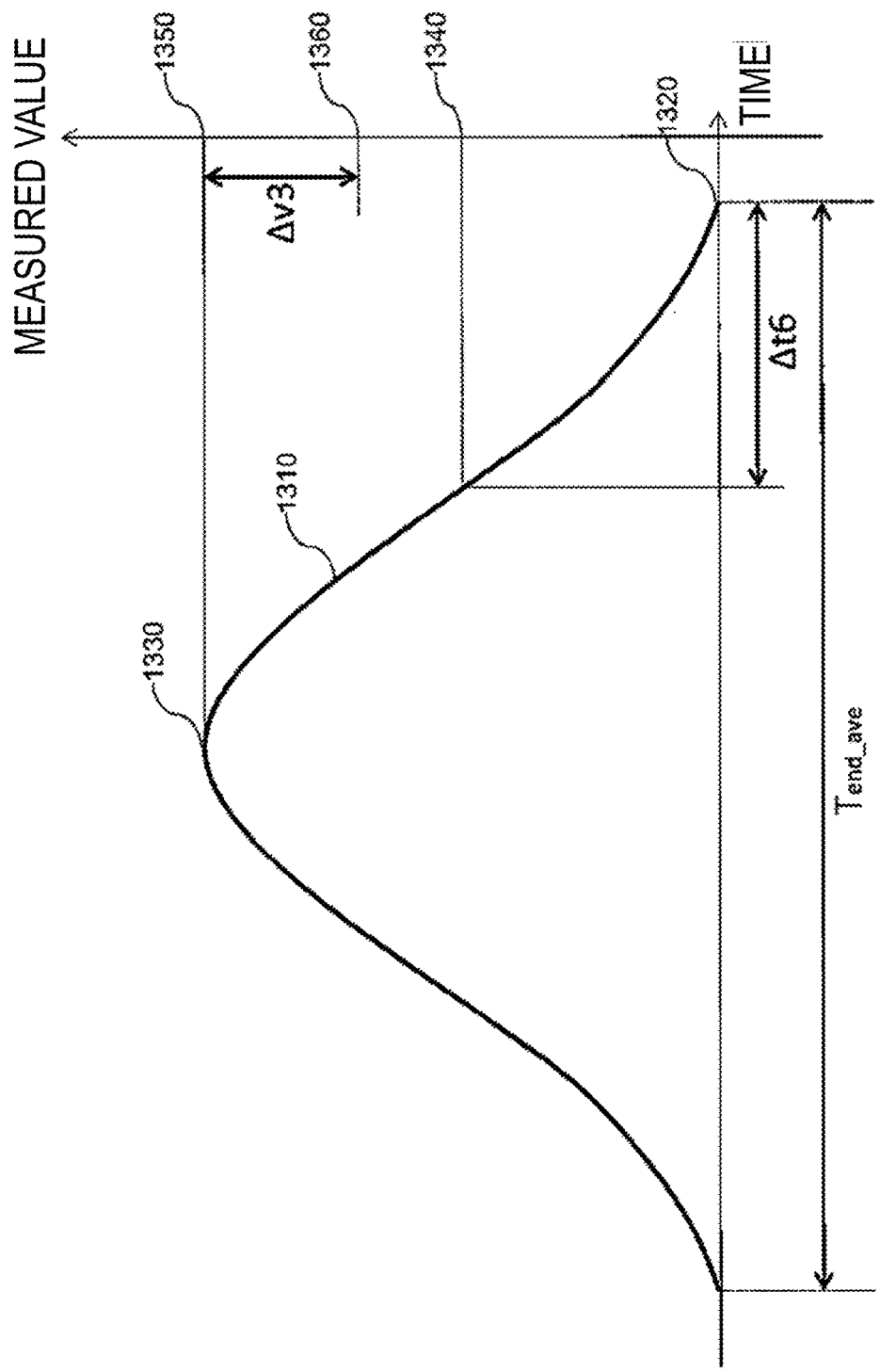
FIG. 13 is a graph for showing an example in which the timing when supplying power is stopped or a period of time in which the power continues to be supplied is set.

7-2-6 Example where Timing when Supplying Power is Stopped or Period of Time in which Power Continues to be Supplied are Set Hereinafter, an example where the timing when supplying the power is stopped or the period of time in which the power continues to be supplied are set will be described in detail with reference to FIG. 13. In FIG. 13, reference numeral 1310 denotes a puff profile, reference numeral 1320 denotes an end point of the changes, and reference numeral 1330 denotes a maximum point of the changes. It should be noted that the puff profile represented in FIG. 13 is intended to be based on the average of the measured values for controlling the power supplied which are obtained in periods of multiple cycles, but is a simplified example for purposes of illustration. Hereinafter, the end point of the changes is the first feature point, and the maximum point of the changes is the second feature point.

The controller 130 calculates an end time $t_{end}$ (i) of the changes with reference to any time, e.g., a start time of the changes, every period from when supplying the power is started to when supplying the power is stopped. Next, the controller 130 obtains an average value $t_{end\_ave}$ of a plurality of end times $t_{end}$ (i) of changes, and calculates deviations $(t_{end\_ave}-t_{end}$ (i)) among the end times $t_{end}$ (i) of changes every period. Then, the controller 130 calculates a value based on the plurality of deviations $(t_{end\_ave}-t_{end}$ (i), and compares the value with a threshold, and when the value is equal to or smaller than the threshold, the controller 130 regards a value (measured value for controlling the power supplied) 1340 on the puff profile 1310 at the time when a given value Δt6 being longer than or equal to zero is subtracted from the average value $t_{end\_ave}$ of a plurality of end times $t_{end}$ (i) of changes as the above-described third threshold Thre3. On the other hand, when the value based on the plurality of deviations $(t_{end\_ave}-t_{end}$ (i)) is not smaller than or equal to the threshold, the controller 130 regards a value 1360 obtained by subtracting a given value Δv3 being equal to or larger than zero from the maximum value 1350 (maximum value of the measured values for controlling the power supplied) 1350 as the above-described third threshold Thre3. By setting the third threshold Thre3 as described above, the timing when supplying the power is stopped or the period of time in which the power continues to be supplied are indirectly set. Note that examples of the value based on the plurality of deviations $(t_{end\_ave}-t_{end}$ (i)) include standard deviation and mean deviation.

Note that in the present embodiment, to set the timing when supplying the power is stopped or the period of time in which the power continues to be supplied, either the end point 1320 or the maximum point 1330 of changes of the puff profile is used. Alternatively, the timing when supplying the power is stopped or the period of time in which the power continues to be supplied may be set using both of the end point 1320 and the marinum point 1330 of changes of the puff profile. By way of example, the timing when supplying the power is stopped may be provided between the end point 1320 and the maximum point 1330 of changes of the puff profile. In other words, the power may continue to be supplied until any time between the end point 1320 and the maximum point 1330 of changes of the puff profile.

8 Seventh Exemplary Operations of Controller 130

The seventh exemplary operations are premised on the controller 130 which performs the operations similar to the fifth exemplary operations. However, in the seventh exemplary operations, the seventh condition is a condition that the measured value from the inhalation sensor 106 for controlling the power supplied is equal to or larger than the sixth threshold Thre6. In the seventh exemplary operations, it is not essential that the eighth condition is severer than the seventh condition, but the eighth condition comprises a plurality of conditions including a condition that the measured value for controlling the power supplied is less than the seventh threshold Thre7 which is larger than the sixth threshold Thre6. When all of the plurality of conditions are satisfied, the process proceeds to step S1108.

In the seventh exemplary operations, the controller 130 stores the profile of the measured values for controlling the power supplied, and updates one of the sixth threshold Thre6 and the seventh threshold Thre7 based on the stored profile of the measured values for controlling the power supplied. In other words, in the seventh exemplary operations, one of the sixth threshold Thre6 and the seventh threshold Thre7 is a constant value, and the other is an updatable value.

Note that the sixth threshold Thre6 may correspond to the above-described first threshold Thre1 or the second threshold Thre2 as a constant value, and the seventh threshold Thre7 may correspond to the above-described third threshold Thre3 which is updatable based on the stored profile of the measured values for controlling the power supplied.

9 Eighth Exemplary Operations of Controller 130

The eighth exemplary operations are premised on the controller 130 which performs the operations similar to the seventh exemplary operations. However, in the seventh exemplary operations, it is not essential to store the profile of the measured values for controlling the power supplied, and it is not essential that one of the sixth threshold Thre6 and the seventh threshold Thre7 is a constant value.

In the eighth exemplary operations, the controller 130 updates one of the sixth threshold Thre6 and the seventh threshold Thre7 at different frequencies than the other. In other words, in the eighth exemplary operations, an update frequency of the sixth threshold Thre6 is different from that of the seventh threshold Thre7.

Note that the update frequency of the sixth threshold Thre6 may be lower than that of the seventh threshold Thre7. The update frequency of the sixth threshold Thre6 being lower than that of the seventh threshold Thre7 includes the situation in which while the sixth threshold Thre6 is constant without being updated, the seventh threshold Thre7 is updated.

10 Ninth Exemplary Operations of Controller 130

The ninth exemplary operations are premised on the controller 130 which performs the operations similar to the sixth exemplary operations.

In the ninth exemplary operation, the controller 130 stores a profile of the measured values representing the first physical quantities for controlling the power supplied, the profile corresponding to the power supply cycle including a period from when the power source starts supplying the power to when supplying the power is stopped, and controls the power supplied in the N-th power supply cycle based on a profile of the measurement values, the profile corresponding to one or more power supply cycles of an the N-1st power supply cycle and power supply cycles before the N-1st power supply cycle. Note that N is a natural number of 2 or more.

REFERENCE SIGNS LIST

100 . . . Aerosol generating device, 102 . . . Reservoir, 104 . . . Atomizer, 106 . . . Inhalation sensor, 108 . . .

Air intake flow path, 110 . . . Aerosol flow path, 112 . . . Wick, 114 . . . Battery, 116 . . . Mouthpiece member, 130 . . . Controller, 135 . . . Power controller, 140 . . . Memory

The invention claimed is:

1. An aerosol generating device, comprising:
   a battery;
   a container that retains liquid;
   an atomizer including a porous ceramic structure that holds the liquid at a position and heats the liquid when power is supplied to the atomizer;
   a pressure sensor; and
   a controller;
   wherein the controller is configured to:
   increase an amount of power supplied from the battery to the atomizer based on a signal output by the pressure sensor indicating that criteria for triggering generation of the aerosol by the atomizer has been satisfied; and
   stop power supply from the battery to the atomizer:
   based on a signal output by the pressure sensor indicating that the criteria for triggering generation of the aerosol by the atomizer is no longer satisfied, and
   after a time condition that is triggered by an output of the pressure sensor is satisfied.

2. An aerosol generating device, comprising:
   a battery;
   a container that retains liquid;
   an atomizer including a porous ceramic structure that holds the liquid at a position and heats the liquid when power is supplied to the atomizer;
   a pressure sensor; and
   a controller;
   wherein the controller is configured to:
   initiate power supply from the battery to the atomizer based on:
   a signal output by the pressure sensor indicating that criteria for triggering generation of the aerosol has been satisfied, and
   a predetermined amount of time having passed from receiving the signal output by the pressure sensor.

3. The aerosol generating device according to claim 2, wherein the controller is further configured to:
   control power supply from the battery to the atomizer based on a puff profile corresponding to changes in measured values over a period of time; and
   wherein the predetermined amount of time is based on the puff profile.

4. The aerosol generating device according to claim 3 wherein the puff profile includes a starting time and ending time.

5. An aerosol generating device, comprising:
   a battery;
   a container that retains liquid;
   an atomizer including a porous ceramic structure that holds the liquid at a position and heats the liquid when power is supplied to the atomizer;
   a pressure sensor; and
   a controller;
   wherein the controller is configured to:
   stop power supply from the battery to the atomizer:
   based on a signal output value by the pressure sensor indicating to pass a maximum value of the pressure sensor, and
   before a change of the value is completed.

6. An aerosol generating device, comprising:
   a battery;
   a container that retains liquid;
   an atomizer including a porous ceramic structure that holds the liquid at a position and heats the liquid when power is supplied to the atomizer;
   a pressure sensor; and
   a controller;
   wherein the controller is configured to:
   stop power supply from the battery to the atomizer after a value which the pressure sensor detects from a user passes a maximum value and before a change of the value is completed.

* * * * *